United States Patent
Lau et al.

(10) Patent No.: US 9,630,988 B2
(45) Date of Patent: Apr. 25, 2017

(54) METHOD FOR PREPARING A COMPOSITION COMPRISING HIGHLY CONCENTRATED ANTIBODIES BY ULTRAFILTRATION

(75) Inventors: Kelby Lau, San Francisco, CA (US); Jean Bender, Gaithersburg, MD (US); Saeko Tanaka, Tokyo (JP); Rumiko Wakayama, Tokyo (JP); Hidenari Yamada, Tokyo (JP); Tomonori Isoda, Tokyo (JP); Masayoshi Oh-Eda, Tokyo (JP)

(73) Assignees: Chugai Seiyaku Kabushiki Kaisha, Tokyo (JP); Genentech, Inc., South San Francisco, CA (US)

( * ) Notice: Subject to any disclaimer, the term of this patent is extended or adjusted under 35 U.S.C. 154(b) by 286 days.

(21) Appl. No.: 14/241,567

(22) PCT Filed: Aug. 31, 2012

(86) PCT No.: PCT/JP2012/005536
§ 371 (c)(1),
(2), (4) Date: May 9, 2014

(87) PCT Pub. No.: WO2013/031237
PCT Pub. Date: Mar. 7, 2013

(65) Prior Publication Data
US 2015/0037319 A1    Feb. 5, 2015

Related U.S. Application Data

(60) Provisional application No. 61/530,158, filed on Sep. 1, 2011.

(51) Int. Cl.
| | |
|---|---|
| *C07K 1/34* | (2006.01) |
| *B01D 61/14* | (2006.01) |
| *B01D 61/22* | (2006.01) |
| *B01D 71/82* | (2006.01) |
| *A61K 39/395* | (2006.01) |
| *C07K 16/28* | (2006.01) |

(52) U.S. Cl.
CPC .......... *C07K 1/34* (2013.01); *A61K 39/39591* (2013.01); *B01D 61/145* (2013.01); *B01D 61/22* (2013.01); *C07K 16/2866* (2013.01); *B01D 2311/14* (2013.01); *B01D 2311/165* (2013.01); *B01D 2315/14* (2013.01); *B01D 2321/02* (2013.01)

(58) Field of Classification Search
None
See application file for complete search history.

(56) References Cited

U.S. PATENT DOCUMENTS

| | | | |
|---|---|---|---|
| 5,219,999 A | 6/1993 | Suzuki et al. | |
| 6,375,847 B1 | 4/2002 | Hartmann | |
| 2003/0013172 A1* | 1/2003 | Gerendash | C12N 9/2417 435/189 |
| 2004/0167320 A1 | 8/2004 | Couto et al. | |
| 2006/0051347 A1 | 3/2006 | Winter et al. | |
| 2006/0246004 A1* | 11/2006 | Adams | C07K 16/2887 424/1.49 |
| 2007/0116700 A1 | 5/2007 | Liu et al. | |
| 2009/0214522 A1 | 8/2009 | Winter | |
| 2010/0190965 A1 | 7/2010 | Yamaguchi et al. | |

FOREIGN PATENT DOCUMENTS

| | | |
|---|---|---|
| EP | 1623752 A2 | 2/2006 |
| JP | 64-043305 A | 2/1989 |
| JP | 03-271234 A | 12/1991 |
| JP | 2002-500164 A | 1/2002 |
| JP | 2005-530845 A | 10/2005 |
| JP | 2008-512473 A | 4/2008 |
| JP | 2010-047527 A | 3/2010 |
| WO | WO 99/19343 A1 | 4/1999 |
| WO | WO 02/00331 A2 | 1/2002 |
| WO | WO 04/001007 A2 | 12/2003 |
| WO | WO 2006/031560 A2 | 3/2006 |
| WO | WO 2008/156124 A1 | 12/2008 |
| WO | WO 2010/111378 A1 | 9/2010 |

OTHER PUBLICATIONS

Luo et al., "High-Concentration UF/DF of a Monoclonal Antibody," BioProcess International, Feb. 2006, 4:44-46.
Kim et al., "Fouling mechanisms of membranes during protein ultrafiltration," Journal of Membrane Science, 1992, 68:79-91.
Liu et al., "Reversible Self-Association Increases the Viscosity of a Concentrated Monoclonal Antibody in Aqueous Solution," Journal of Pharmaceutical Sciences, Sep. 2005, 94(9):1928-1940.
Shiloach et al., "Tangential Flow Filtration," Adv. Biotechnol. Processes, 1988, 8:97-125.
Shire et al., "Challenges in the Development of High Protein Concentration Formulations," Journal of Pharmaceutical Sciences, Jun. 2004, 93(6):1390-1402.
Shire, Steven J., "Formulation and manufacturability of biologics," Current Opinion in Biotechnology, 2009, 20:708-714.
Suki et al., "Flux decline in protein ultrafiltration," Journal of Membrane Society, 1984, 21:269-283.
Suki et al., "Modeling Fouling Mechanisms in Protein Ultrafiltration," Journal of Membrane Society, 1986, 27:181-193.
Turker et al., "Membrane Fouling in a Constant-Flux Ultrafiltration Cell," Journal of Membrane Science, 1987, 34:267-281.
van Reis et al., "Membrane separations in biotechnology," Current Opinion in Biotechnology, 2001, 12:208-211.
Kagaku Daijiten. (Gengai Roka) 1974, 3:423-424, with English translation.

* cited by examiner

*Primary Examiner* — Daniel E Kolker
*Assistant Examiner* — James Rogers
(74) *Attorney, Agent, or Firm* — Foley & Lardner LLP

(57) ABSTRACT

The present invention provides a method for preparing a composition comprising highly concentrated antibodies by ultrafiltration in batch concentration mode having a first constant feed rate step and a second controlled feed rate step.

29 Claims, 11 Drawing Sheets

METHOD FOR PREPARING A COMPOSITION COMPRISING HIGHLY CONCENTRATED ANTIBODIES BY ULTRAFILTRATION

TECHNICAL FIELD

The present invention relates to the field of biological science, more specifically to the field of an antibody preparation. In particular, the present invention relates to a method for preparing a composition comprising highly concentrated antibodies by ultrafiltration. The method used in the present invention enables antibody therapies to attain high concentration formulations at ambient temperature, such as above 100 g/L, preferably above 200 g/L, particularly preferably above 250 g/L.

BACKGROUND ART

There is a growing demand for highly concentrated low volume formulations of antibody therapies for subcutaneous administration, especially in the field of chronic disease therapy, to improve patient convenience and compliance by offering outpatient treatment.

For antibody drug substance manufacturing, ultrafiltration/diafiltration (UF/DF) is typically the final process step. Ultrafiltration is a membrane-based separation process that separates molecules in solution on the basis of size. Diafiltration is a specific type of ultrafiltration in which an aqueous buffer is added to the retentate. In this step, purified drug substance is concentrated and exchanged to protein concentration and excipient composition necessary for drug product formulation.

The predominant technology used in the industry for ultrafiltration/diafiltration (UF/DF) process is a form of tangential flow filtration (TFF) (see generally, Shiloach J. et al., 1988, Van Reis R. et al., 2001). In this technology, protein solution is recirculated under pressure, tangentially to an ultrafiltration membrane. This TFF approach works well for drug substance at low to moderate concentrations and in most cases a UF/DF process for one antibody is highly adaptable to another antibody with minimal changes. However, in situations with high protein concentrations, has come a series of technical challenges in process performance (see generally, Shire S J. et al., 2004, Luo R. et al., 2006, Shire S J., 2009).

The attainment of high concentration formulations by TFF technology can be difficult because highly concentrated protein solutions may lead to limited mass transfer due to decreased flux and eventual membrane fouling (see for example, Suki A. et al., 1984, 1986, Kim K J. et al., 1992). While that can be overcome by increasing the membrane surface area or replacing the membrane, it can lead to a lower yield. Another limitation is high viscosity may lead to high feed pressure, exceeding upper limit for membrane integrity during the process (see for example, Turker M. et al., 1987, Liu J. et al., 2005). While an implementation of an appropriate formulation design such as increase of ionic strength or addition of particular compounds can help decrease viscosity (see for example, Liu J. et al., 2006), it may be a challenging exercise to decrease the viscosity while ensuring the stable formulation composition. In situation where greater decreases in viscosity are required, it can be addressed by processing at elevated temperatures (see for example, Winter C., 2009). However, in such cases, protein stability may be compromised by prolonged exposure to higher temperatures. The problem to be solved by the present invention is therefore to provide a novel processing method to achieve high protein concentration by manipulating other processing parameters.

CITATION LIST

Patent Literature

[PTL 1] Liu J, Shire S J. Reduced-viscosity concentrated protein formulations. US Patent Dec. 15, 2006, US20070116700 A1

[PTL 2] Winter C. Process for concentration of antibodies and therapeutic products thereof. US Patent Feb. 19, 2009, US20090214522 A1

Non Patent Literature

[NPL 1] Kim K J, Fane A G, Fell C J D, Joy D C. Fouling mechanisms of membranes during protein ultrafiltration, J. Membr. Sci. 68 (1992) 79.

[NPL 2] Liu J, Nguyen M D H, Andya J D, Shire S J. Reversible selfassociation increases the viscosity of a concentrated monoclonal antibody in aqueous solution. J Pharm Sci (2005), 94:1928-1940.

[NPL 3] Luo R, Waghmare R, Krishnan M, Adams C, Poon E, Kahn D. High concentration UF/DF of a monoclonal antibody. Strategy for optimization and scale-up, Bio-Process Int. 4 (2006) 44.

[NPL 4] Shiloach J, Martin N, Moes H. Tangential flow filtration. Adv Biotechnol Process (1988), 8:97-125.

[NPL 5] Shire S J, Shahrokh Z, Liu J. Challenges in the development of high protein concentration formulations. J Pharm Sci (2004), 93:1390-1402.

[NPL 6] Shire S J. Formulation and manufacturability of biologics. Curr Opin Biotechnol (2009), 20:708-714

[NPL 7] Suki A, Fane A G, Fell C J D. Flux decline in protein ultrafiltration, J. Membr. Sci. 21 (1984) 269.

[NPL 8] Suki A, Fane A G, Fell C J D. Modeling fouling mechanisms in protein ultrafiltration, J. Membr. Sci. 27 (1986) 181.

[NPL 9] Turker M, Hubble J. Membrane fouling in a constant-flux ultrafiltration cell, J. Membr. Sci. 34 (1987) 267.

[NPL 10] Van Reis R, Zydney A. Membrane separations in biotechnology. Curr Opin Biotechnol (2001), 12:208-211.

SUMMARY OF INVENTION

The industry standard technology for concentrating proteins at manufacturing scale is ultrafiltration by tangential flow. Key challenges for products with high final concentrations are to prevent membrane fouling and to overcome high feed pressure.

In general terms, the present disclosure describes the specific manipulation of process parameters for successful concentration of proteins, such as an antibody preparation, pharmaceutical formulations containing such a preparation, and their use in human therapy or animal therapy.

In embodiments the present disclosure provides a method wherein a feed flow rate is maintained at a high flow rate until an optimal protein concentration then reduced to a lower value to continue further concentrating. For example, concentration is performed at a feed flow rate equal or greater than 200 LMH until the retentate solution is concentrated to a protein concentration greater than 200 g/L, where a feed pressure builds up to 85-100% of the specified maximum feed pressure of an ultrafiltration membrane, then further concentration is continued at a feed flow rate equal or less than 120 LMH. The attainable protein concentration within the operational limits is higher than the conventional process comprising either one step with a constant feed flow rate or two steps with a step-down feed flow control on early transition.

The present disclosure also provides, in embodiments, a more preferable method wherein a feed flow rate is maintained as high as possible until the end of the concentration process. For example, a feed flow rate is automatically controlled in a manner to maintain a feed pressure within 85-100% of the specified maximum feed pressure of an ultrafiltration membrane once a feed pressure reaches 85-100% of the specified maximum feed pressure of an ultrafiltration membrane under a constant feed flow rate.

The present disclosure also provides, in embodiments, the effectiveness of a circulation step inserted in the middle of a concentration process. For example, 20 minutes circulation at a feed flow rate of 10-80 LMH is inserted once a feed pressure reaches 85-100% of the specified maximum feed pressure of an ultrafiltration membrane under a constant feed flow rate. This circulation step can mitigate the feed pressure buildup during a subsequent ultrafiltration process.

In summary, it is an object of the present invention to provide the following [1] to [33].

[1] A method for preparing a composition comprising highly concentrated antibodies by ultrafiltration, wherein the method comprises the steps of:
1) regulating a feed flow rate to allow the value of feed pressure applied to an ultrafiltration membrane to increase to 85-100% of a specified maximum feed pressure of an ultrafiltration membrane; and
2) decreasing the feed flow rate to maintain or decrease the value of the feed pressure applied to the ultrafiltration membrane after the step (1).
[2] The method of [1], wherein the antibody preparation is processed at ambient temperature.
[3] The method of [1], wherein the antibody preparation is processed at a temperature from 10 to 30 degrees C.
[4] The method of [1], wherein the antibody preparation is processed at a temperature from 15 to 30 degrees C.
[5] The method of [1], wherein the highly concentrated antibodies have a high concentration of above 100 g/L or a viscosity above 2 mPa·s.
[6] The method of [1], wherein the highly concentrated antibodies have a high concentration of above 200 g/L or a viscosity above 10 mPa·s.
[7] The method of [1], wherein the highly concentrated antibodies have a high concentration of above 250 g/L or a viscosity above 40 mPa·s.
[8] The method of [1], wherein the feed flow rate in step (1) is maintained at 200 LMH (L/m$^2$/hour) or higher.
[9] The method of [1], wherein the feed flow rate in step (1) is maintained at 250 LMH (L/m$^2$/hour) or higher.
[10] The method of [1], [8] and [9], wherein the feed flow rate in step (1) is maintained at a constant rate.
[11] The method of [1], wherein the maximum value of the feed pressure applied to an ultrafiltration membrane in step (1) is from 2.0 bar to 4.0 bar.
[12] The method of [1], wherein the maximum value of the feed pressure applied to an ultrafiltration membrane in step (1) is 3.5 bar.
[13] The method of [1], wherein the maximum value of the feed pressure applied to an ultrafiltration membrane in step (1) is 85-100% of the specified maximum feed pressure of the ultrafiltration membrane.
[14] The method of [1], wherein step (1) is transitioned to step (2) when the retentate solution is concentrated to a protein concentration greater than 200 g/L.
[15] The method of [1], wherein step (1) is transitioned to step (2) when the retentate solution is concentrated to a protein concentration equal or greater than 220 g/L.
[16] The method of [1], wherein step (1) is transitioned to step (2) when the retentate solution is concentrated to a protein concentration equal to 240 g/L.
[17] The method of [13], wherein the feed flow rate after the value of the feed pressure is decreased in step (2) is maintained at a constant rate.
[18] The method of [13] or [17], wherein the feed flow rate after the value of the feed pressure is decreased in step (2) is maintained at 120 LMH (L/m$^2$/hour) or lower.
[19] The method of [13] or [17], wherein the feed flow rate after the value of the feed pressure is decreased in step (2) is maintained at 80 LMH (L/m$^2$/hour) or lower.
[20] The method of [1], wherein the value of the feed pressure applied to an ultrafiltration membrane in step (2) is maintained at a constant value.
[21] The method of [1], wherein the value of the feed pressure applied to an ultrafiltration membrane in step (2) is maintained within 85-100% of the specified maximum feed pressure of the ultrafiltration membrane by ramping down a feed flow rate.
[22] The method of [20] or [21], wherein the feed flow rate is automatically regulated in a manner to maintain the feed pressure within 85-100% of the specified maximum feed pressure of the ultrafiltration membrane by a feedback control between a feed pressure and a feed flow rate.
[23] The method of [1], further comprising between step (1) and step (2), the following step of:
3) recirculating the antibody preparation through the membrane with a permeate valve closed.
[24] The method of [23], wherein the antibody preparation is recirculated with a retentate pressure control valve fully open.
[25] The method of [23], wherein the feed flow rate in step (3) is maintained at a constant flow rate between 5 to 120 LMH (L/m$^2$/hour).
[26] The method of [23], wherein the feed flow rate in step (3) is maintained at a constant flow rate between 10 to 80 LMH (L/m$^2$/hour).
[27] The method of [1], wherein the buffer composition of the antibody preparation is between 10 to 30 mmol/L histidine.
[28] The method of [1], wherein the buffer composition of the antibody preparation is 20 mmol/L histidine.
[29] The method of [1], wherein the pH of the antibody preparation is between pH 3.0 and pH 10.0.
[30] The method of [1], wherein the pH of the antibody preparation is between pH 5.5 and pH 6.5.
[31] The method of [1], wherein the pH of the antibody preparation is pH 6.0.
[32] The method of [1], wherein the ultrafiltration membrane has a molecular weight cut off of 50 kDa or less.
[33] The method of [1], wherein the ultrafiltration membrane has a molecular weight cut off of 30 kDa or less.
[34] The method of [1], wherein the composition comprises highly concentrated anti-human interleukin-6 receptor monoclonal antibodies.
[35] The method of [34], wherein the composition comprises highly concentrated tocilizumab.
[36] A liquid composition which comprises highly concentrated antibodies prepared by the method of [1].

[37] A pharmaceutical liquid composition which comprises highly concentrated antibodies prepared by the method of [1] and a pharmaceutically acceptable carrier.

[38] A method for preparing a composition comprising highly concentrated proteins by ultrafiltration, wherein the method comprises the steps of:
1) regulating a feed flow rate to allow the value of feed pressure applied to an ultrafiltration membrane to increase to 85-100% of a specified maximum feed pressure of an ultrafiltration membrane; and
2) decreasing the feed flow rate to maintain or decrease the value of the feed pressure applied to the ultrafiltration membrane after the step (1).

It will also be understood that both the foregoing summary of the present invention and the following detailed description are of exemplified embodiments, and not restrictive of the present invention or other alternate embodiments of the present invention. Other objects and features of the invention will become more fully apparent when the following detailed description is read in conjunction with the accompanying figures and examples. In particular, while the invention is described herein with reference to a number of specific embodiments, it will be appreciated that the description is illustrative of the invention and is not constructed as limiting of the invention. Various modifications and applications may occur to those who are skilled in the art, without departing from the spirit and the scope of the invention, as described by the appended claims. Likewise, other objects, features, benefits and advantages of the present invention will be apparent from this summary and certain embodiments described below, and will be readily apparent to those skilled in the art. Such objects, features, benefits and advantages will be apparent from the above in conjunction with the accompanying examples, data, figures and all reasonable inferences to be drawn therefrom, alone or with consideration of the references incorporated herein.

BRIEF DESCRIPTION OF DRAWINGS

Various aspects and applications of the present invention will become apparent to the skilled artisan upon consideration of the brief description of the figures and the detailed description of the present invention and its preferred embodiments that follows.

DESCRIPTION OF EMBODIMENTS

Figure 1:
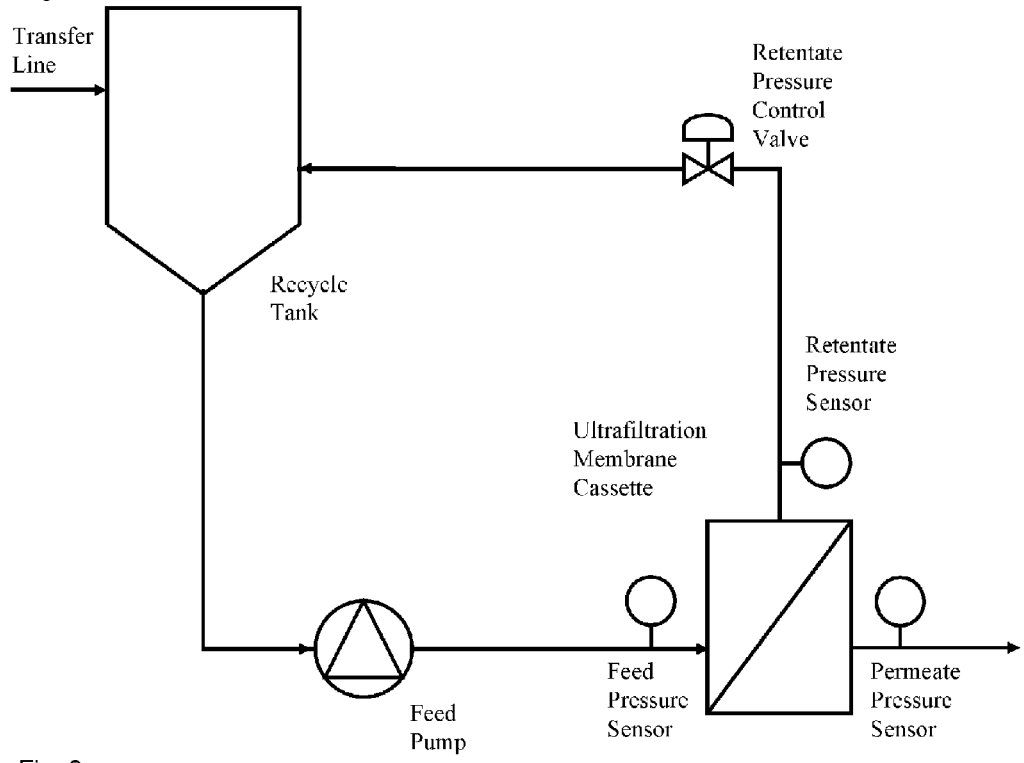
FIG. 1 demonstrates an apparatus for UF/DF process, in embodiments of the present disclosure.

Although any methods and materials similar or equivalent to those described herein can be used in the practice or testing of embodiments of the present invention, the preferred methods are now described. However, before the present methods are described, it is to be understood that the present invention is not limited to the particular sizes, shapes, dimensions, materials, methodologies, protocols, etc. described herein, as these may vary in accordance with routine experimentation and optimization. It is also to be understood that the terminology used in the description is for the purpose of describing the particular versions or embodiments only, and is not intended to limit the scope of the present invention which will be limited only by the appended claims.

The disclosure of each publication, patent or patent application mentioned in this specification is specifically incorporated by reference herein in its entirety. However, nothing herein is to be construed as an admission that the invention is not entitled to antedate such disclosure by virtue of prior invention.

Unless otherwise defined, all technical and scientific terms used herein have the same meaning as commonly understood by one of ordinary skill in the art to which the present invention belongs. In case of conflict, the present specification, including definitions, will control. In addition, the materials, methods, and examples are illustrative only and not intended to be limiting.

The present invention relates to a method for preparing a composition comprising highly concentrated antibodies by ultrafiltration.

The present invention comprises a method for preparing a composition comprising highly concentrated antibodies by ultrafiltration wherein a feed flow rate and a feed pressure applied to an ultrafiltration membrane are variable and changed during a filtration process.

Particularly preferred embodiments of the present invention are set forth below.

A method for preparing a composition comprising highly concentrated antibodies by ultrafiltration, wherein the method comprises the steps of:

1) regulating a feed flow rate to allow the value of feed pressure applied to an ultrafiltration membrane to increase to 85-100% of a specified maximum feed pressure of an ultrafiltration membrane; and 2) decreasing the feed flow rate to maintain or decrease the value of the feed pressure applied to the ultrafiltration membrane after the step (1).

The term "ultrafiltration" which is used within the present invention denotes a membrane-based separation process that separates molecules in solution on the basis of size. The term "tangential flow filtration (TFF)" denotes a specific filtration method wherein a fluid flows tangentially to a membrane. The solution containing protein molecules is concentrated by flowing along, i.e. tangential to, the surface of an ultrafiltration membrane under pressure. The ultrafiltration membrane has a pore size with a certain cut off value. In one embodiment the cut off value is in the range of 50 kDa or less, preferably of 30 kD or less.

The term "feed flow" denotes the flow of fluid from the feed pump to the membrane. The term "feed flow rate" denotes the volumetric rate of flow of the solution to the membrane. The feed flow rate is usually given in terms of volume per unit time as liter/minute and normalized in terms of volume per unit membrane area per unit time as liter/m$^2$/h (LMH). The term "flux" denotes the normalized permeate flow through the membrane in terms of volume per unit membrane area per unit time as liter/m$^2$/h (LMH).

The term "feed pressure" denotes the pressure applied to the inlet of an ultrafiltration membrane. The expression "maximum feed pressure" denotes the acceptable maximum value of the feed pressure which is specified by a vendor as a product specification of the ultrafiltration membrane. The term "retentate pressure" denotes the pressure applied to the outlet of an ultrafiltration membrane. The term "permeate pressure" denotes the pressure applied to the permeate side of the ultrafiltration membrane. The term "transmembrane pressure (TMP)" denotes the pressure which drives the fluid to filtrate across an ultrafiltration membrane. The value of TMP can be calculated as:

$$TMP=(P_{feed}+P_{retentate})/2-P_{permeate}$$

TMP is an average of the feed pressure and the retentate pressure in the case where the permeate side is open in the TFF equipment. The value of pressure is usually given in terms of "bar" or "MPa" or "psi".

The term "antibody" refers to a protein specifically recognizing an antigen. The antibody may be monoclonal or polyclonal. The antibody may exist in a variety of formats, including, for example, Fv, Fab, and F(ab)2 as well as single chains (scFv) or diabodies. Furthermore, any fragment or modification (e.g., chimeric antibody, humanized antibody, etc.) of the antibody may be used for the present method. Methods to prepare these kinds of antibodies are well known in the art, and any method may be employed in the present invention to prepare such antibodies and fragments thereof.

The monoclonal antibodies used in the present invention include not only those derived from animals such as humans, mice, rats, hamsters, rabbits, sheep, camels, and monkeys, but also artificially modified gene recombinant antibodies such as chimeric antibodies, humanized antibodies, and bispecific antibodies. The antibodies of the present invention also include gene recombinant antibodies that result from artificially modifying the antibody constant regions to alter the physical properties of the antibody molecule (specifically, alteration of the isoelectric point (pI), improvement of the affinity for Fc receptor, etc) for the purpose of improving the blood persistence and in vivo pharmacokinetics.

The immunoglobulin class of the antibodies used in the present invention is not particularly limited; and the class may be any class, including IgG such as IgG1, IgG2, IgG3, and IgG4, IgA, IgD, IgE, and IgM. However, IgG and IgM are preferred.

Antibodies used in the present invention include, but are not limited to, anti-tissue factor antibodies, anti-IL-6 receptor antibodies, anti-IL-6 antibodies, anti-HM1.24 antigen monoclonal antibodies, anti-parathyroid hormone-related peptide antibodies (anti-PTHrP antibodies), anti-glypican-3 antibodies, anti-ganglioside GM3 antibodies, anti-TPO receptor agonist antibodies, antibodies as a functional substitute for coagulation factor VIII, anti-IL31 receptor antibodies, anti-HLA antibodies, anti-AXL antibodies, anti-CXCR4 antibodies, anti-NR10 antibodies, and bispecific antibodies against factor IX and factor X.

Preferred humanized antibodies used in the present invention include anti-humanized interleukin 6 (IL-6) receptor antibodies (tocilizumab, hPM-1, and MRA) (see WO 92/19759), humanized anti-HM1.24 antigen monoclonal antibodies (see WO 98/14580), humanized anti-parathyroid hormone-related peptide antibodies (anti-PTHrP antibodies) (see WO 98/13388), humanized anti-tissue factor antibodies (see WO 99/51743), humanized anti-glypican-3 IgG1kappa antibodies (see PCT/JP05/013103), and anti-NR10 humanized antibodies (see WO2009/072604). Particularly preferred humanized antibodies used in the present invention are humanized anti-IL-6 receptor antibodies.

Preferred human IgM antibodies include recombinant human anti-ganglioside GM3 IgM antibodies (see WO 05/05636).

Preferred minibodies include anti-TPO receptor agonist diabodies (see WO 02/33072) and anti-CD47 agonist diabodies (see WO 01/66737).

Furthermore, antibodies with an improved isoelectric point include, for example, Mab1 which is an anti-IL-6 receptor antibody described in WO 2011/090088 (H chain/SEQ ID NO: 1 therein; L chain/SEQ ID NO: 2 therein), and fully humanized NS22 antibody, which is an anti-NR10 humanized antibody, produced by the method described in Example 12 of WO2009/072604.

The present invention also relates to a method for preparing a composition comprising highly concentrated proteins other than antibodies by ultrafiltration. The present invention comprises a method for preparing a composition comprising highly concentrated proteins by ultrafiltration wherein a feed flow rate and a feed pressure applied to an ultrafiltration membrane are variable and changed during a filtration process. The proteins used in the present invention include, but are not limited to, enzymes, cytokines, and peptide aptamers.

The expression "a composition comprising highly concentrated antibodies" as used within the present application denotes an aqueous, buffered solution containing the highly concentrated antibodies. The term "buffer" as used within the present application denotes a solution in which changes of pH due to the addition or release of acidic or basic substances is leveled by a buffer substance. Any buffer substance resulting in such an effect can be used. In one embodiment pharmaceutically acceptable buffer substances are used, such as e.g. phosphoric acid or salts thereof, acetic acid or salts thereof, citric acid or salts thereof, morpholine or salts thereof, 2-(N-morpholino) ehanesulfonic acid or salts thereof, or tris (hydroxymethyl) aminomethane (TRIS) or salts thereof. In a preferred embodiment the buffer composition of the antibody preparation is between 10 to 30 mmol/L histidine. In more preferred embodiment the buffer composition of the antibody preparation is 20 mmol/L histidine.

Optionally the buffered solution may comprise an additional salt, such as e.g. sodium chloride, and/or sodium sulphate, and/or potassium chloride, and/or potassium sulfate, and/or sodium citrate, and/or potassium citrate.

In one embodiment of the present invention, the pH of the antibody preparation is between pH 3.0 and pH 10.0, preferably between pH 5.5 and pH 6.5, more preferred pH 6.0.

In one embodiment of the present invention, the antibody preparation is processed at ambient temperature, preferably at a temperature from 10 to 30 degrees C., more preferred at a temperature from 15 to 30 degrees C.

In one embodiment, the highly concentrated antibodies have a protein concentration of above 100 g/L or a viscosity above 2 mPa·s. In a preferred embodiment, the highly concentrated antibodies have a protein concentration of above 200 g/L or a viscosity above 10 mPa·s. In more preferred embodiment, the highly concentrated antibodies have a protein concentration of above 250 g/L or a viscosity above 40 mPa·s.

In one embodiment, the feed flow rate in step (1) is maintained at 200 LMH (L/m$^2$/hour) or higher. In a preferred embodiment, the feed flow rate in step (1) is maintained at 250 LMH (L/m$^2$/hour) or higher. In these embodiments the feed flow rate in step (1) is preferably maintained at a constant rate.

In one embodiment, the maximum value of the feed pressure applied to an ultrafiltration membrane in step (1) is within 85-100% of the specified maximum feed pressure of the ultrafiltration membrane. In a preferred embodiment, the maximum value of the feed pressure is from 2.0 bar to 4.0 bar. In a more preferred embodiment, the maximum value of the feed pressure applied to an ultrafiltration membrane in step (1) is 3.5 bar.

In one embodiment, step (1) is transitioned to step (2) when the retentate solution is concentrated to a protein concentration greater than 200 g/L. In a preferred embodiment, step (1) is transitioned to step (2) when the retentate solution is concentrated to a protein concentration equal or greater than 220 g/L. In a more preferred embodiment, step (1) is transitioned to step (2) when the retentate solution is concentrated to a protein concentration equal to 240 g/L.

In this embodiment, the feed flow rate after the value of the feed pressure is decreased in step (2) is maintained at a constant rate, preferably 120 LMH (L/m$^2$/hour) or lower, or more preferred 80 LMH (L/m$^2$/hour) or lower.

In one embodiment, the value of the feed pressure applied to the ultrafiltration membrane in step (2) is maintained at a constant value.

In one embodiment, the value of the feed pressure applied to the ultrafiltration membrane in step (2) is maintained within 85-100% of the specified maximum feed pressure of the ultrafiltration membrane by ramping down the feed flow rate.

In one embodiment, the feed flow rate is automatically regulated in a manner to maintain the feed pressure within 85-100% of the specified maximum feed pressure of the ultrafiltration membrane by a feedback control between a feed pressure and a feed flow rate.

In one embodiment of the production method according to the present invention further comprises between step (1) and step (2), the following step of:

3) recirculating the antibody preparation through the membrane with a permeate valve closed.

In this embodiment, the antibody preparation is recirculated with a retentate pressure control valve fully open.

In this embodiment, the feed flow rate in step (3) is preferably maintained at a constant flow rate between 5 to 120 LMH (L/m$^2$/hour), and more preferably between 10 to 80 LMH (L/m$^2$/hour).

The present invention also relates to a liquid composition that comprises highly concentrated antibodies prepared by the methods of the present invention.

The present invention also relates to pharmaceutical liquid compositions. The pharmaceutical liquid compositions of the present invention may include pharmaceutically acceptable carriers.

In the present invention, pharmaceutical liquid compositions ordinarily refer to agents for treating, preventing, testing, or diagnosing diseases.

The pharmaceutical liquid compositions of the present invention can be formulated by methods known to those skilled in the art. For example, they can be used parenterally, in the form of injections of sterile solutions or suspensions including water or other pharmaceutically acceptable liquid. For example, such liquid compositions may be formulated by mixing in the form of unit dose required in the generally approved medicine manufacturing practice by appropriately combining with pharmaceutically acceptable carriers or media, specifically with sterile water, physiological saline, vegetable oil, emulsifier, suspension, surfactant, stabilizer, flavoring agent, excipient, vehicle, preservative, binder, or such. In such formulations, the amount of active ingredient is adjusted to obtain an appropriate amount in a pre-determined range.

Sterile compositions for injection can be formulated using vehicles such as distilled water for injection, according to standard formulation practice.

Aqueous solutions for injection include, for example, physiological saline and isotonic solutions containing dextrose or other adjuvants (for example, D-sorbitol, D-mannose, D-mannitol, and sodium chloride). It is also possible to use in combination appropriate solubilizers, for example, alcohols (ethanol and such), polyalcohols (propylene glycol, polyethylene glycol, and such), non-ionic surfactants (polysorbate 80™, HCO-50, and such).

Oils include sesame oil and soybean oils. Benzyl benzoate and/or benzyl alcohol can be used in combination as solubilizers. It is also possible to combine buffers (for example, phosphate buffer and sodium acetate buffer), soothing agents (for example, procaine hydrochloride), stabilizers (for example, benzyl alcohol and phenol), and/or antioxidants. Appropriate ampules are filled with the prepared injections.

The pharmaceutical liquid compositions of the present invention are preferably administered parenterally. For example, the liquid compositions may be in the dosage form for injections, transnasal administration, transpulmonary administration, or transdermal administration. For example, they can be administered systemically or locally by intravenous injection, intramuscular injection, intraperitoneal injection, subcutaneous injection, or such.

Administration methods can be appropriately selected in consideration of the patient's age and symptoms. The dose of a pharmaceutical liquid composition containing an antigen-binding molecule may be, for example, from 0.0001 to 1000 mg/kg for each administration. Alternatively, the dose may be, for example, from 0.001 to 100,000 mg per patient. However, the present invention is not limited by the numeric values described above. The doses and administration methods vary depending on the patient's weight, age, symptoms, and such. Those skilled in the art can set appropriate doses and administration methods in consideration of the factors described above.

EXAMPLES

The following examples serve to more fully describe the manner of using the above-described disclosure, as well as to set forth the best modes contemplated for carrying out various aspects of the disclosure. It is understood that these examples in no way serve to limit the true scope of this disclosure, but rather are presented for illustrative purpose.

Comparative Example 1

FIG. 1 illustrates the major components of an apparatus used to perform an ultrafiltration process. A recycle tank contains initial material and retentate. A mixing apparatus ensures uniform mixing between the initial pool added via a transfer line and the retentate that returns back to the recycle tank from ultrafiltration membrane. A feed pump creates tangential flow over the membrane. Feed pressure is measured at the inlet of the membrane. A retentate pressure control valve is used on the retentate side, downstream of the membrane, to adjust a retentate pressure, for example under transmembrane pressure (TMP) control. Between the membrane and the retentate pressure control valve, a pressure sensor measures a retentate pressure. On the permeate side of the membranes, a pressure of the liquid filtered through the membrane is monitored by a permeate pressure sensor.

For lab-scale ultrafiltration processing an automated TFF system AKTAcrossflow (GE Healthcare, US) was used. The ultrafiltration process was performed using a 0.02 m$^2$ Sartocon slice cassette with a Hydrosart membrane of regenerated cellulose, a nominal molecular weight cut-off of 30 kDa and a maximum feed pressure specification of 4.0 bar (Sartorius, Germany).

Prior to use, the membrane cassette was cleaned with 1 mol/L sodium hydroxide and rinsed with purified water. The normalized flux was determined to ensure comparable membrane properties. The membrane cassette was equilibrated with 30 mmol/L histidine buffer pH 5.8 prior to process. Ultrafiltration was operated at ambient temperature.

The starting material was prepared from a purified pool of a humanized anti-human interleukin-6 receptor (IL-6R) monoclonal antibody (tocilizumab (registered trade mark: ACTEMRA, RoACTEMRA) see PCT Pub. No. WO92/19759, U.S. Pat. No. 5,795,965). The purified pool was concentrated up to 60 mg/mL and buffer exchanged into 30 mmol/L histidine buffer pH 5.8.

The buffer exchanged pool (DF pool) was loaded into the TFF system with 625 g antibody/m$^2$. The feed flow rate was set to a constant rate of 250 LMH (L/m$^2$/hour) during the entire process. The TMP was controlled at 1.0 bar until the retentate pressure control valve came to a fully open. The ultrafiltration process was operated with the permeate side open-ended. The operation was terminated when the feed pressure exceeded 3.5 bar. After ultrafiltration processing, the concentrated solution was circulated with the permeate side closed for 15 minutes under a constant retentate flow rate of 10 mL/min and then recovered into a graduated cylinder. The recovered pool was stirred until visually homogeneous.

For protein concentration measurement, the recovered pool was diluted gravimetrically using a density value measured by a density meter DMA 4500 (Anton Paar, Austria). UV absorbance at 280 nm was measured with a UV/Vis spectrophotometer DU800 (Beckman Coulter, US).

Figure 2:
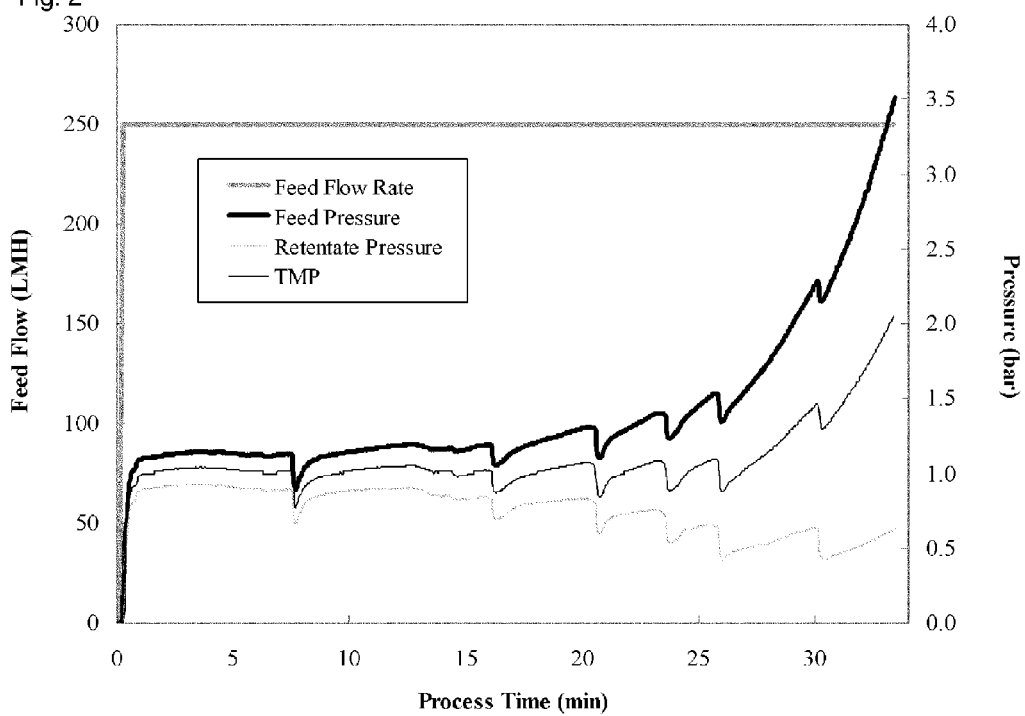
FIG. 2 demonstrates the measured process values over time for the feed flow rate, feed pressure, retentate pressure, TMP at lab scale. The feed flow rate was set to a constant rate of 250 LMH (L/m$^2$/hour) during the entire process.

FIG. 2 shows the measured process values over time for the feed flow rate, feed pressure, retentate pressure, TMP. Table 1 shows the result of protein concentration measurement.

TABLE 1

|  | Protein concentration (g/L) |
| --- | --- |
| DF pool | 53.0 |
| Recovered pool | 209 |

Comparative Example 2

Comparative Example 1 was repeated with the following exception. The feed flow rate was reduced to 80 LMH when the retentate volume reached the value that corresponds to protein concentration of 100 g/L.

Figure 3:
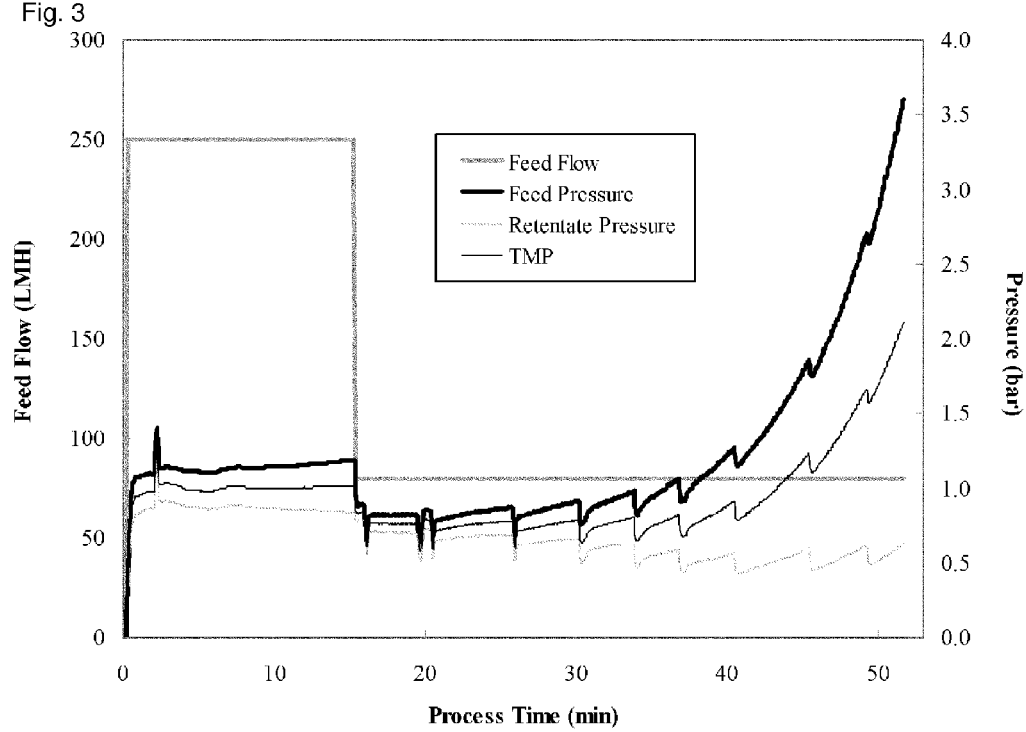
FIG. 3 demonstrates the measured process values over time for the feed flow rate, feed pressure, retentate pressure, TMP at lab scale. The feed flow rate was reduced to 80 LMH when the retentate volume reached the value that corresponds to protein concentration of 100 g/L.

FIG. 3 shows the measured process values over time for the feed flow rate, feed pressure, retentate pressure, TMP. Table 2 shows the result of protein concentration measurement.

TABLE 2

| | Protein concentration (g/L) |
|---|---|
| DF pool | 51.2 |
| Recovered pool | 230 |

Comparative Example 3

Comparative Example 1 was repeated with the following exception. The feed flow rate was reduced to 80 LMH when the retentate volume reached the value that corresponds to protein concentration of 200 g/L.

Figure 4:
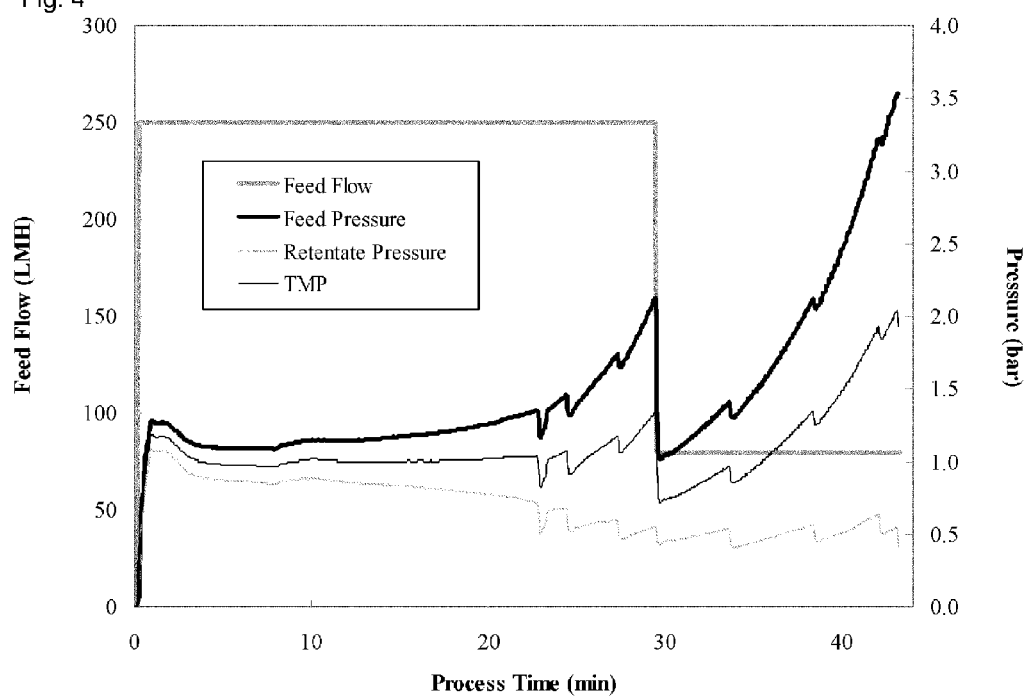
FIG. 4 demonstrates the measured process values over time for the feed flow rate, feed pressure, retentate pressure, TMP at lab scale. The feed flow rate was reduced to 80 LMH when the retentate volume reached the value that corresponds to protein concentration of 200 g/L.

FIG. 4 shows the measured process values over time for the feed flow rate, feed pressure, retentate pressure, TMP. Table 3 shows the result of protein concentration measurement.

TABLE 3

| | Protein concentration (g/L) |
|---|---|
| DF pool | 51.2 |
| Recovered pool | 227 |

Example 4

Comparative Example 1 was repeated with the following exception. The feed flow rate was reduced to 80 LMH when the feed pressure exceeded 3.5 bar. The value of the retentate volume at that point corresponds to protein concentration of 240 g/L.

Figure 5:
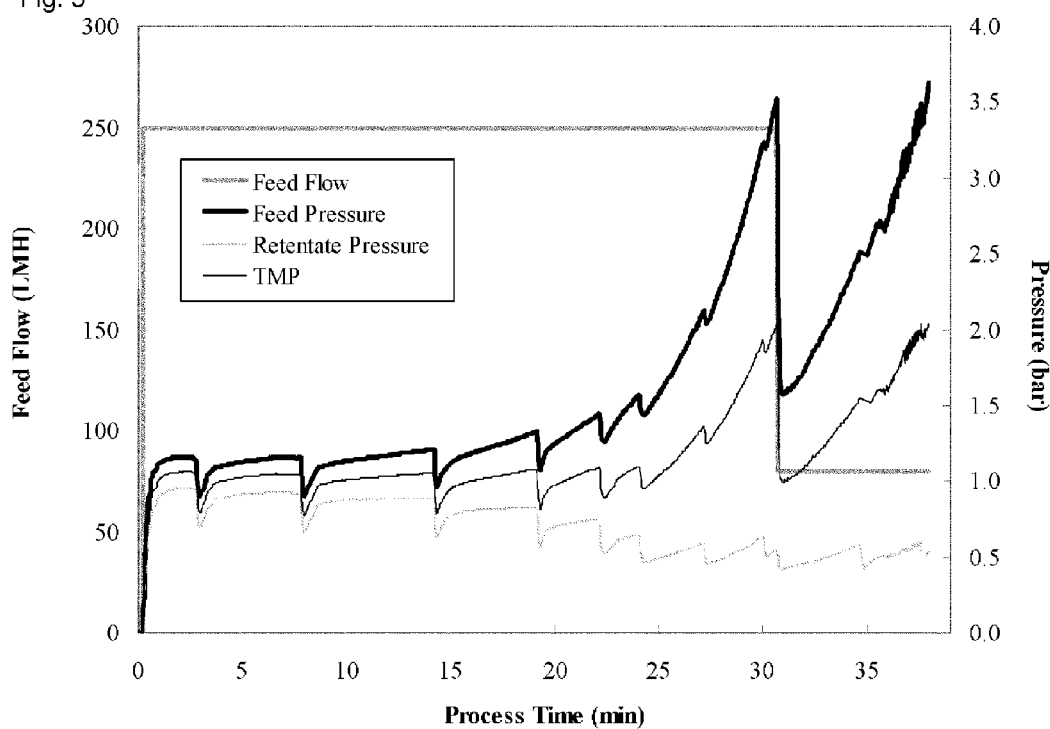
FIG. 5 demonstrates the measured process values over time for the feed flow rate, feed pressure, retentate pressure, TMP at lab scale. The feed flow rate was reduced to 80 LMH when the feed pressure exceeded 3.5 bar, which corresponded to protein concentration of 240 g/L.

FIG. 5 shows the measured process values over time for the feed flow rate, feed pressure, retentate pressure, TMP. Table 4 shows the result of protein concentration measurement.

TABLE 4

| | Protein concentration (g/L) |
|---|---|
| DF pool | 49.5 |
| Recovered pool | 263 |

Example 5

Example 4 was repeated with the following exception. Once the feed pressure exceeded 3.5 bar under a constant feed flow rate of 250 LMH, the feed flow rate was set to automatic flow control in a manner to maintain the feed pressure of 3.5 bar. The operation was terminated when the feed flow rate decreased to 80 LMH.

Figure 6:
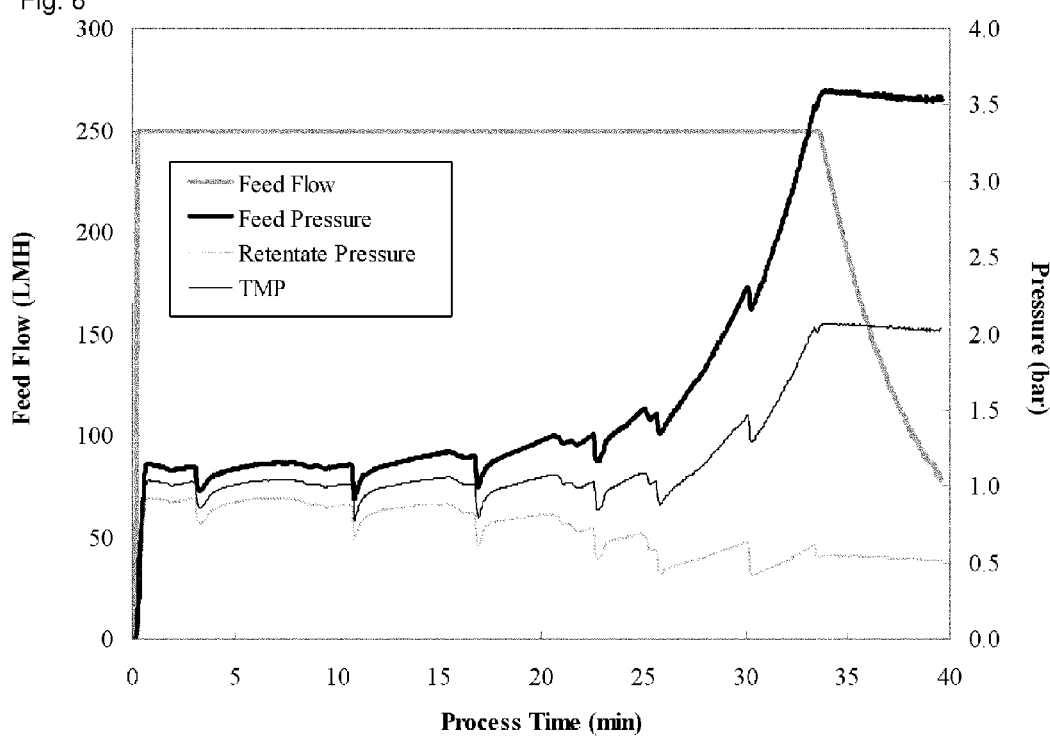
FIG. 6 demonstrates the measured process values over time for the feed flow rate, feed pressure, retentate pressure, TMP at lab scale. Once the feed pressure exceeded 3.5 bar under a constant feed flow rate of 250 LMH, the feed flow rate was set to automatic flow control in a manner to maintain the feed pressure of 3.5 bar. The operation was terminated when the feed flow rate decreased to 80 LMH.

FIG. 6 shows the measured process values over time for the feed flow rate, feed pressure, retentate pressure, TMP. Table 5 shows the result of protein concentration measurement.

TABLE 5

| | Protein concentration (g/L) |
|---|---|
| DF pool | 51.2 |
| Recovered pool | 273 |

Example 6

Example 4 was repeated with the following exception. The flow path was switched into the mode of circulation once the feed pressure exceeded 3.5 bar. In the circulation mode, the retentate was circulated through the membrane with the retentate pressure control valve fully open and the permeate closed. After the circulation for 20 minutes under a constant feed flow rate of 80 LMH, ultrafiltration was resumed under the same feed flow rate.

Figure 7:
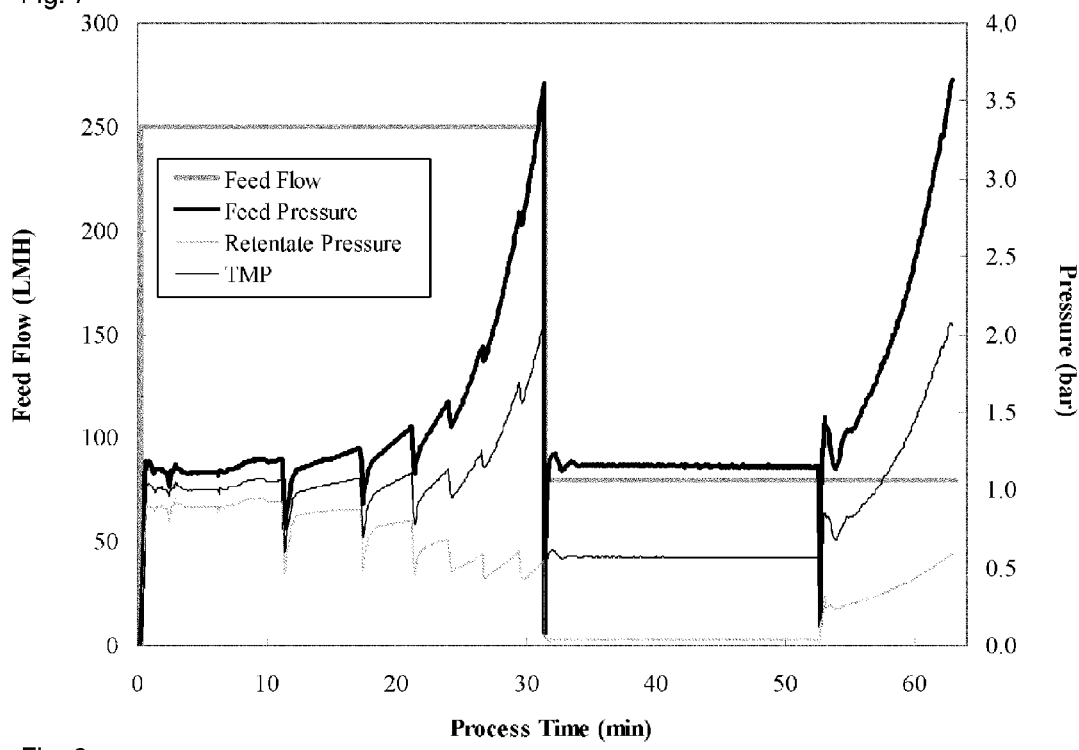
FIG. 7 demonstrates the measured process values over time for the feed flow rate, feed pressure, retentate pressure, TMP at lab scale. The flow path was switched into the mode of circulation once the feed pressure exceeded 3.5 bar. After the circulation for 20 minutes under a constant feed flow rate of 80 LMH, ultrafiltration was resumed under the same feed flow rate.

FIG. 7 shows the measured process values over time for the feed flow rate, feed pressure, retentate pressure, TMP. Table 6 shows the result of protein concentration measurement.

TABLE 6

| | Protein concentration (g/L) |
|---|---|
| DF pool | 50.0 |
| Recovered pool | 268 |

Example 7

Example 6 was repeated with the following exception. The circulation was performed under a constant feed flow rate of 10 LMH.

Figure 8:
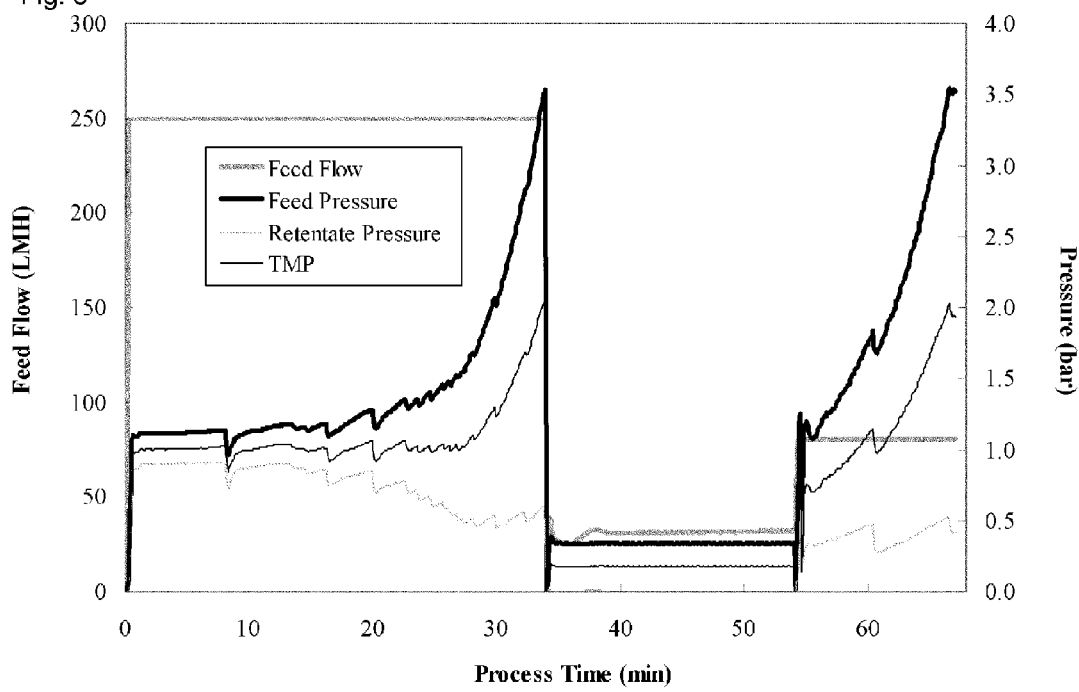
FIG. 8 demonstrates the measured process values over time for the feed flow rate, feed pressure, retentate pressure, TMP at lab scale. The circulation was performed under a constant feed flow rate of 10 LMH.

FIG. 8 shows the measured process values over time for the feed flow rate, feed pressure, retentate pressure, TMP. TABLET shows the result of protein concentration measurement.

TABLE 7

| | Protein concentration (g/L) |
|---|---|
| DF pool | 51.7 |
| Recovered pool | 270 |

Figure 9:
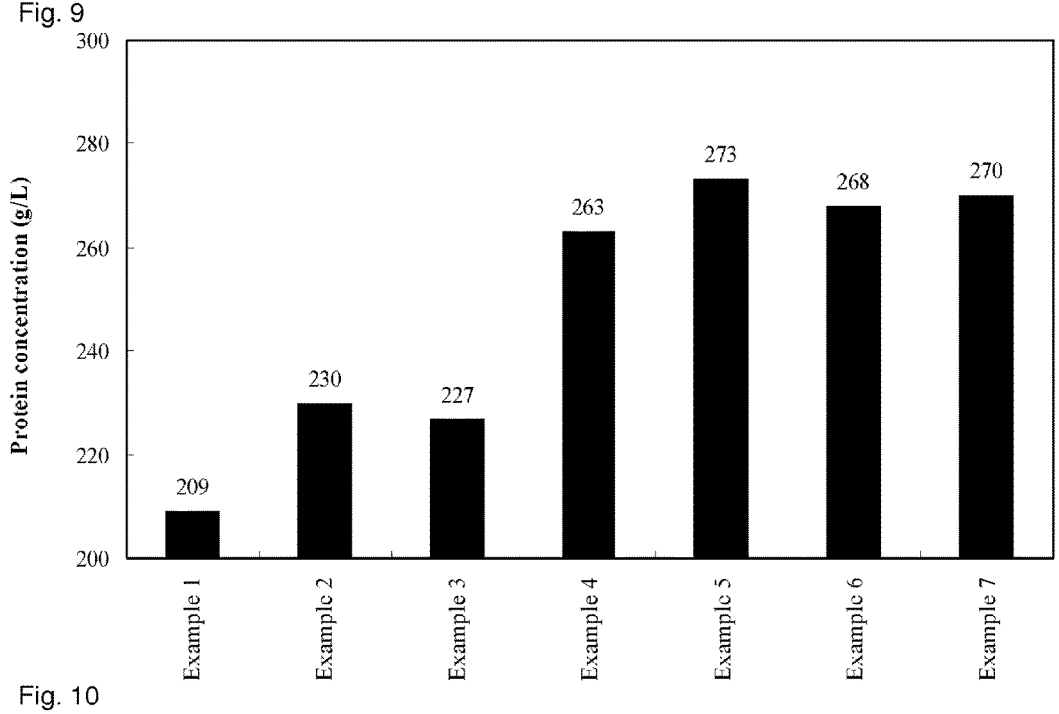
FIG. 9 summarizes the protein concentration of the recovered pool at lab scale, in embodiments of the present disclosure.

FIG. 9 summarizes the concentration of the recovered pool in Examples 1-7.

Example 8

The viscosity of a concentrated pool of a humanized IL-6R monoclonal antibody was measured using a AR1000 rheometer and a cone and plate geometry with 40 mm diameter, 2 degree angle and 53 micrometer truncation (TA Instruments, US).

Figure 10:
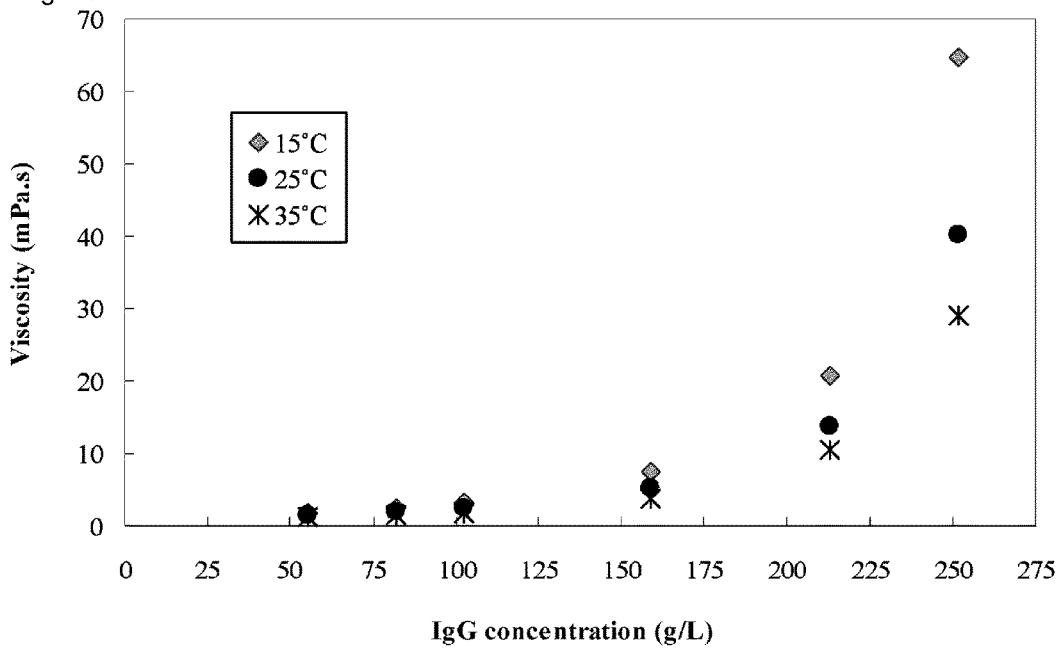
FIG. 10 demonstrates the viscosity profile of a concentrated humanized IL-6R monoclonal antibody, in embodiments of the present disclosure.

FIG. 10 shows the plot of viscosity against concentration at temperatures of 15 degrees C., 25 degrees C. and 35 degrees C.

Comparative Example 9

For a scale-up study, the UF/DF process was performed at pilot scale. The process was operated in two stages with different sizes of TFF system. A larger TFF system, using 1.20 m$^2$ Sartocon cassettes, was used to process the UF1/DF/UF2 steps. A smaller TFF system, using 0.30 m$^2$ Sartocon cassettes, was used to process the UF3/UF4 steps. The entire process was operated at ambient temperatures with the permeate side open-ended. The Sartocon cassettes used were 30 kDa (cut-off) Hydrosart membranes (Sartorius, Germany).

Prior to use, the membrane cassettes were cleaned with 1 mol/L sodium hydroxide and rinsed with purified water. The normalized flux was determined to ensure comparable membrane properties.

Prior to process, the membrane cassettes were equilibrated with 30 mmol/L histidine buffer pH 5.8 in the large system and 20 mmol/L histidine buffer pH 6.1 in the small system respectively. The whole process was performed at ambient temperature.

In the large system, a purified pool of a humanized anti-human IL-6R monoclonal antibody was loaded with 259 g antibody/m$^2$. The feed flow rate was set to a constant rate of 710 LMH. The TMP was controlled at 1.0 bar. The purified pool was concentrated to 20 g/L in UF1 step and then diafiltered with 7 diavolumes of 30 mmol/L histidine buffer pH 5.8. After the diafiltration, the pool was further concentrated to 60 g/L in UF2 step. The UF2 pool was circulated through the membrane for 15 minutes under a low differential pressure of 5 psi and then recovered into a separate container.

In the small system, the recovered UF2 pool was loaded with 990 g antibody/m$^2$. In UF3 step, the feed flow rate was set to a constant rate of 250 LMH. The UF3 step was ended when the retentate volume reached the value that corresponds to protein concentration of 100 g/L. The feed flow rate was set to a constant rate of 80 LMH in UF4 step. The TMP was controlled at 1.0 bar until the retentate pressure control valve came to a fully open. The operation was terminated when the retentate volume decreased to the value that corresponds to protein concentration of 240 g/L. It is of significant note that the feed flow rate was manually reduced after 80 minutes since the feed pressure was approaching the upper limit before the retentate volume reached the target volume.

The UF4 pool was circulated through the membrane for 15 minutes under a low differential pressure of 15 psi and then recovered into a separate container. The recovered UF4 pool was mixed well by inverting the container.

For protein concentration measurement, the recovered UF4 pool was diluted gravimetrically using a density value measured by a density meter Densito 30PX (Mettler Toledo, Switzerland). UV absorbance at 280 nm was measured with a UV/Vis spectrophotometer UV-1700 (Shimadzu, Japan).

Figure 11:
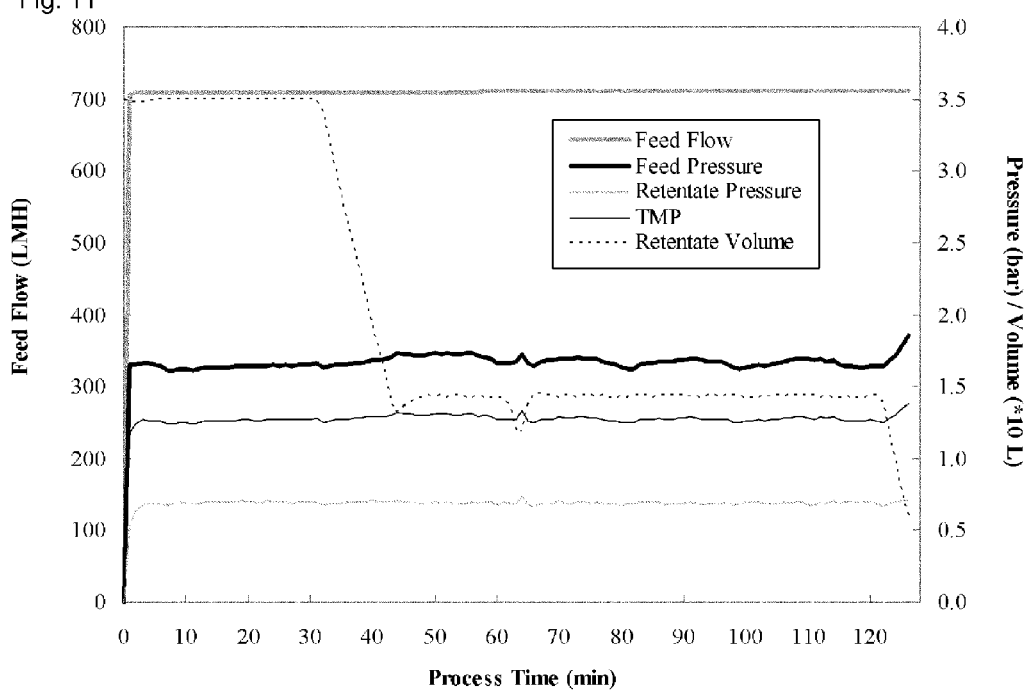
FIG. 11 demonstrates the measured process values over time for the feed flow rate, feed pressure, retentate pressure, TMP and retentate volume in UF1/DF/UF2 steps at pilot scale.

FIG. 11 shows the measured process values over time for the feed flow rate, feed pressure, retentate pressure, TMP and retentate volume in UF1/DF/UF2 steps.

Figure 12:
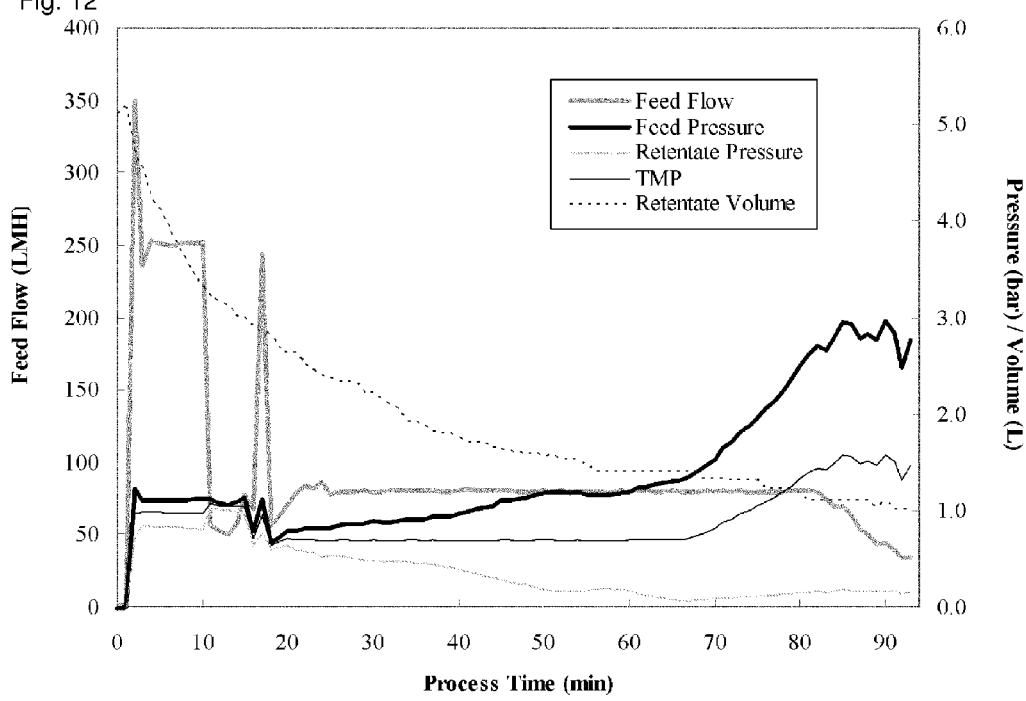
FIG. 12 demonstrates the measured process values over time for the feed flow rate, feed pressure, retentate pressure, TMP and retentate volume in UF3/UF4 steps at pilot scale.

FIG. 12 shows the measured process values over time for the feed flow rate, feed pressure, retentate pressure, TMP in UF3/UF4 steps.

TABLE 8 shows the result of protein concentration measurement.

TABLE 8

| | Protein concentration (g/L) |
|---|---|
| Purified pool | 3.06 |
| Recovered UF2 pool | 63.5 |
| Recovered UF4 pool | 221 |

TABLE 9 shows the result of step yield calculation.

TABLE 9

| | Step Yield (%) |
|---|---|
| Purified pool | N/A |
| Recovered UF2 pool | 98.8 |
| Recovered UF4 pool | 79.8 |

Example 10

Comparative Example 9 was repeated with the following exceptions. UF3/4 steps were performed using 0.40 m$^2$ Sartocon cassettes with a Hydrosart membrane of 30 kDa cut-off (Sartorius, Germany). In the large system, the purified pool was loaded with 274 g antibody/m$^2$. In the small system, the recovered UF2 pool was loaded with 804 g antibody/m$^2$. The process transitioned from UF3 step to UF4 step when the retentate volume reached the value that corresponds to protein concentration of 220 g/L.

Figure 13:
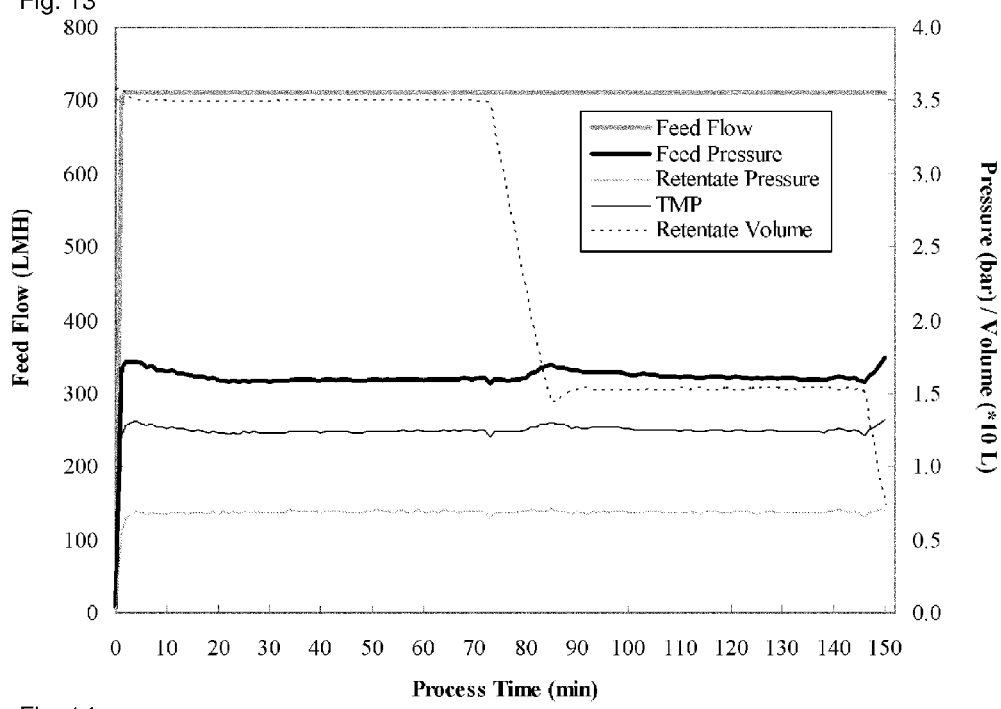
FIG. 13 demonstrates the measured process values over time for the feed flow rate, feed pressure, retentate pressure, TMP and retentate volume in UF1/DF/UF2 steps at pilot scale.

FIG. 13 shows the measured process values over time for the feed flow rate, feed pressure, retentate pressure, TMP and retentate volume in UF1/DF/UF2 steps.

Figure 14:
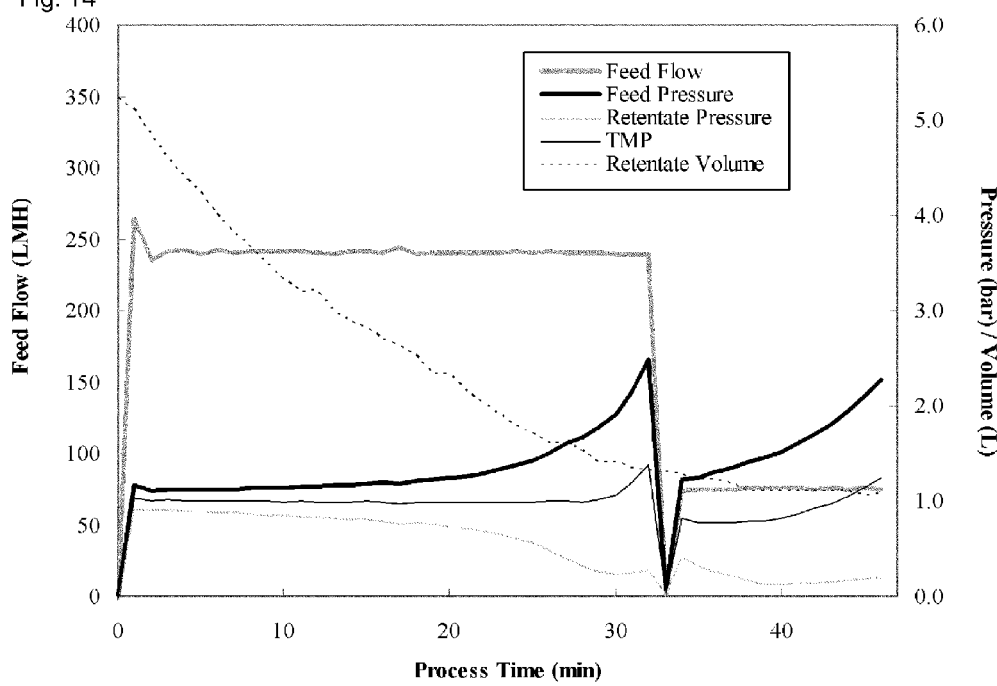
FIG. 14 demonstrates the measured process values over time for the feed flow rate, feed pressure, retentate pressure, TMP and retentate volume in UF3/UF4 steps at pilot scale.

FIG. 14 shows the measured process values over time for the feed flow rate, feed pressure, retentate pressure, TMP and retentate volume in UF3/UF4 steps.

Table 10 shows the result of protein concentration measurement.

TABLE 10

| | Protein concentration (g/L) |
|---|---|
| Purified pool | 1.78 |
| Recovered UF2 pool | 65.6 |
| Recovered UF4 pool | 231 |

Table 11 shows the result of step yield calculation.

TABLE 11

| | Step Yield (%) |
|---|---|
| Purified pool | N/A |
| Recovered UF2 pool | 95.6 |
| Recovered UF4 pool | 93.3 |

Example 11

Example 10 was repeated with the following exceptions. Production scale TFF systems were used in a GMP manufacturing facility. UF1/DF/UF2 steps were performed using 35.10 m$^2$ Sartocon cassettes and UF3/4 steps were using 17.55 m$^2$ Sartocon cassettes with a Hydrosart membrane of 30 kDa cut-off (Sartorius, Germany). In a large system, the purified pool was loaded with 243 g antibody/m$^2$. In a small system, the recovered UF2 pool was loaded with 478 g antibody/m$^2$. DF buffer was changed to 39 mmol/L histidine buffer pH 5.8. The target protein concentration of UF2 pool was increased to 75 g/L. At the end of UF2 step, the feed flow rate was reduced to prevent foaming in the recycle tank. To maximize the recovery, UF2 pool and UF4 pool were recovered with buffer displacement of 70 L and 1 L respectively. The recovered UF4 pool was formulated at 180 g/L in 20 mmol/L histidine buffer pH 6.0, mmol/L methionine, 100 mmol/L arginine and 0.2% polysorbate 80 (see PCT Pub. No. WO 2009/084659). For protein concentration measurement, UF4 pool and recovered UF4 pool were diluted gravimetrically using a density reference. UV absorbance at 280 nm was measured with a UV/Vis spectrophotometer UV-2450 (Shimadzu, Japan).

Figure 15:
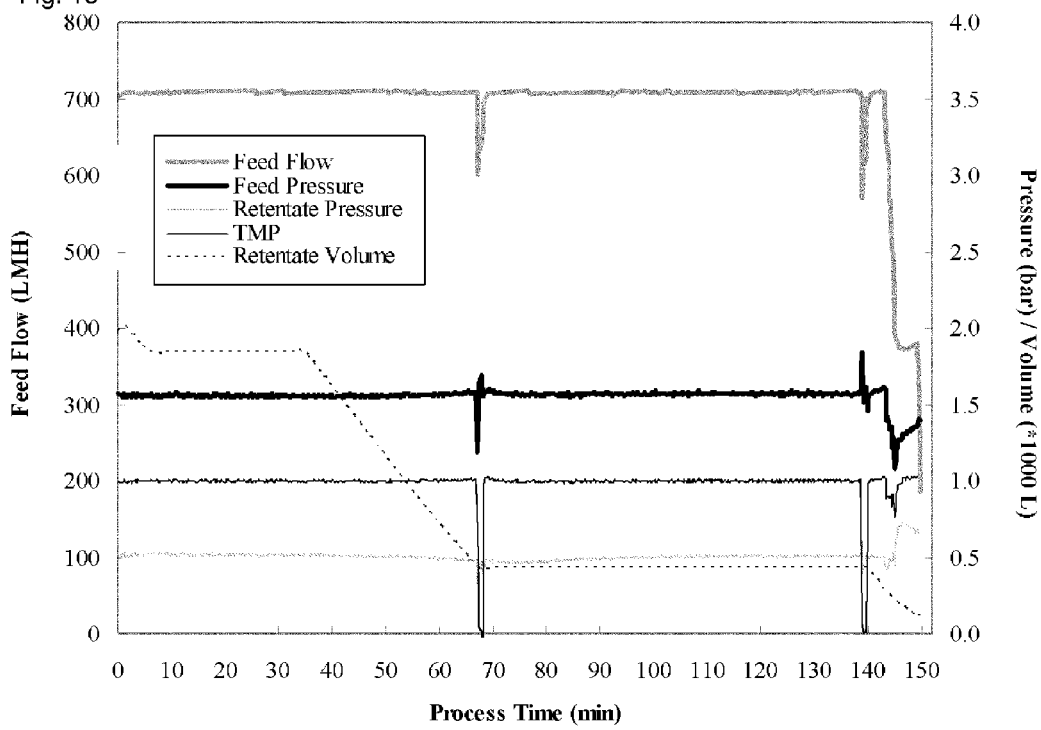
FIG. 15 demonstrates the measured process values over time for the feed flow rate, feed pressure, retentate pressure, TMP and retentate volume in UF1/DF/UF2 steps at manufacturing scale.

FIG. 15 shows the measured process values over time for the feed flow rate, feed pressure, retentate pressure, TMP and retentate volume in UF1/DF/UF2 steps.

Figure 16:
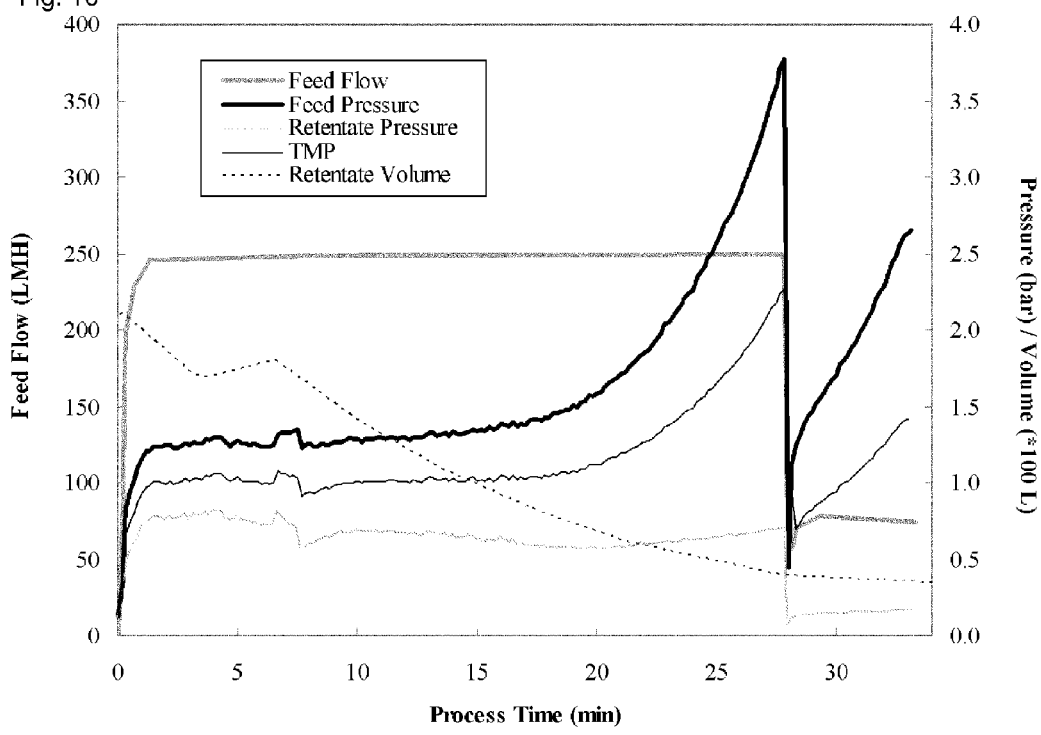
FIG. 16 demonstrates the measured process values over time for the feed flow rate, feed pressure, retentate pressure, TMP and retentate volume in UF3/UF4 steps at manufacturing scale.

FIG. 16 shows the measured process values over time for the feed flow rate, feed pressure, retentate pressure, TMP and retentate volume in UF3/UF4 steps.

Table 12 shows the result of protein concentration measurement.

TABLE 12

|  | Protein concentration (g/L) |
| --- | --- |
| Purified pool | 2.78 |
| UF2 end | 73.2 |
| Recovered UF2 pool | 46.4 |
| UF4 end | 239 |
| Recovered UF4 pool | 231 |
| Formulated bulk | 181 |

Table 13 shows the result of step yield calculation.

TABLE 13

|  | Step Yield (%) |
| --- | --- |
| Purified pool | N/A |
| Recovered UF2 pool | 99.5 |
| Recovered UF4 pool | 90.9 |

The histidine concentration was measured using a HPLC system Alliance 2695 (Waters, US) and a YMC-Pack ODSA, 250×4.6 mm column (YMC, Japan). Table 14 shows the result of histidine quantitation assay.

TABLE 14

|  | Histidine Concentration (mmol/L) |
| --- | --- |
| Recovered UF4 pool | 17.5 |
| Formulated bulk | 19.9 |

The monomer contents in the in-process pools were measured using a HPLC system Alliance 2695 (Waters, US) and a TSK G3000SW$_{XL}$ column (Tosoh, Japan). Table 15 shows the result of SEC assay.

TABLE 15

|  | Monomer (%) |
| --- | --- |
| Purified pool | 99.9 |
| Recovered UF2 pool | 99.9 |
| Formulated bulk | 99.7 |

Example 12

Example 11 was repeated with the following exception. In the large system, the purified pool was loaded with 246 g antibody/m$^2$. In the small system, the recovered UF2 pool was loaded with 482 g antibody/m$^2$.

Figure 17:
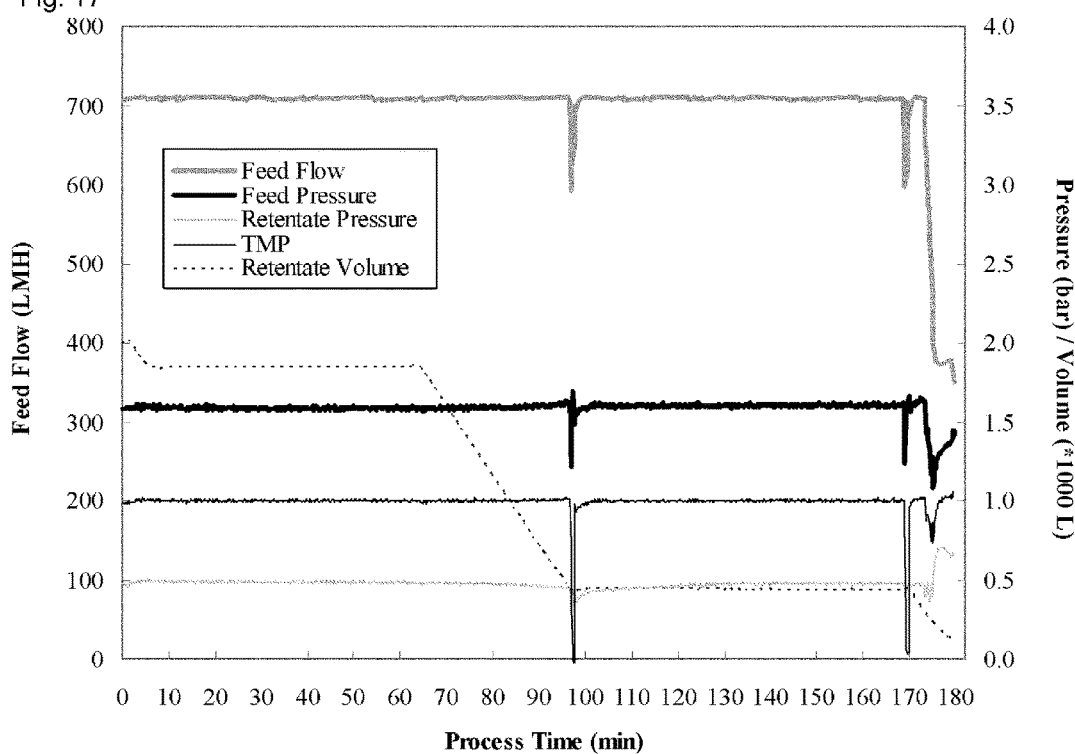
FIG. 17 demonstrates the measured process values over time for the feed flow rate, feed pressure, retentate pressure, TMP and retentate volume in UF1/DF/UF2 steps at manufacturing scale.

FIG. 17 shows the measured process values over time for the feed flow rate, feed pressure, retentate pressure, TMP and retentate volume in UF1/DF/UF2 steps.

Figure 18:
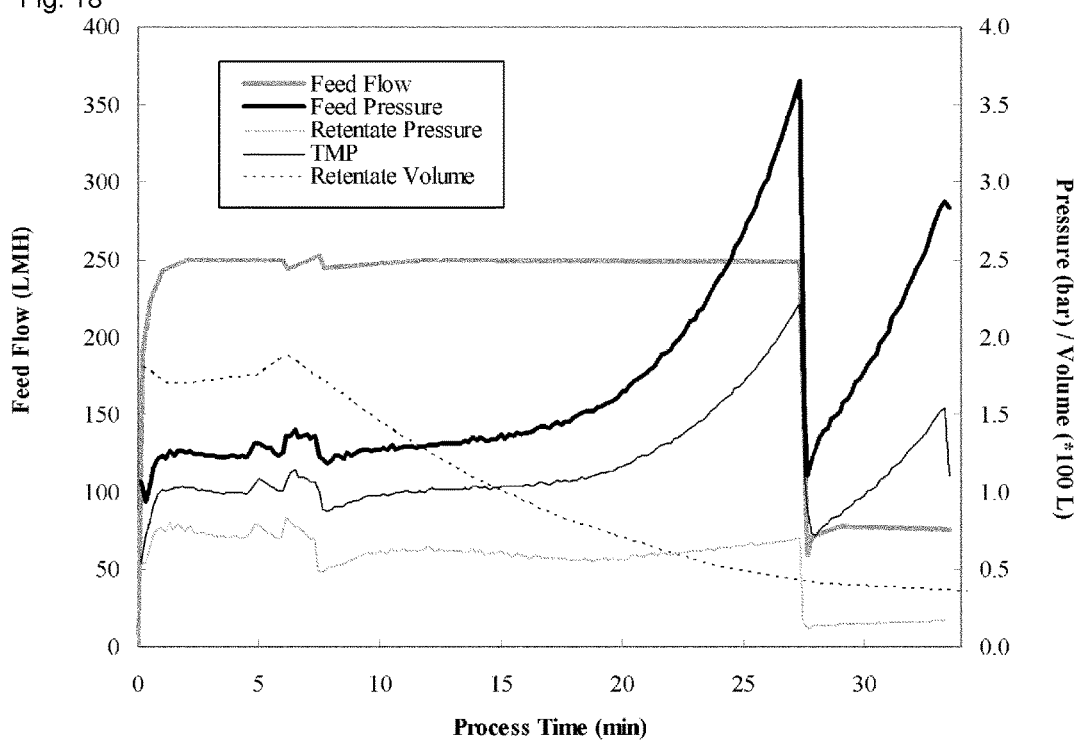
FIG. 18 demonstrates the measured process values over time for the feed flow rate, feed pressure, retentate pressure, TMP and retentate volume in UF3/UF4 steps at manufacturing scale.

FIG. 18 shows the measured process values over time for the feed flow rate, feed pressure, retentate pressure, TMP in UF3/UF4 steps.

Table 16 shows the result of protein concentration measurement.

TABLE 16

|  | Protein concentration (g/L) |
| --- | --- |
| Purified pool | 1.95 |
| UF2 end | 73.7 |
| Recovered UF2 pool | 46.0 |
| UF4 end | 239 |
| Recovered UF4 pool | 231 |
| Formulated bulk | 180 |

Table 17 shows the result of step yield calculation.

TABLE 17

|  | Step Yield (%) |
| --- | --- |
| Purified pool | N/A |
| Recovered UF2 pool | 99.2 |
| Recovered UF4 pool | 94.5 |

The histidine concentration was measured using a HPLC system Alliance 2695 (Waters, US) and a YMC-Pack ODSA, 250×4.6 mm column (YMC, Japan). Table 18 shows the result of histidine quantitation assay.

TABLE 18

|  | Histidine Concentration (mmol/L) |
| --- | --- |
| Recovered UF4 pool | 17.3 |
| Formulated bulk | 19.4 |

The monomer contents in the in-process pools were measured using a HPLC system Alliance 2695 (Waters, US) and a TSK G3000SW$_{XL}$ column (Tosoh, Japan). Table 19 shows the result of SEC assay.

TABLE 19

|  | Monomer (%) |
| --- | --- |
| Purified pool | 99.9 |
| Recovered UF2 pool | 99.9 |
| Formulated bulk | 99.7 |

Comparative Example 13

An automated lab-scale TFF system AKTAcrossflow (GE Healthcare, US) was used for ultrafiltration processing. The ultrafiltration process was performed using two 88 cm$^2$ Pellicon 3 cassettes with Ultracel membranes of regenerated cellulose, a nominal molecular weight cut-off of 30 kDa (Merck Millipore, Germany).

Prior to use, the membrane cassettes were cleaned with 0.5 mol/L sodium hydroxide and rinsed with purified water. The normalized flux was determined to ensure comparable membrane properties. The membrane cassettes were equilibrated with 20 mmol/L tris, 150 mmol/L arginine buffer pH 7.0 prior to process. Ultrafiltration was operated at ambient temperature.

The starting material was prepared from a purified pool of a monoclonal anti-NR10 humanized antibody (fully humanized NS22 antibody prepared according to the method shown in Example 12 of WO 2009/072604) which belongs to the antibody class of IgG2. This is an antibody whose amino acid sequence was modified such that the pI is reduced to 5.6. The purified pool was concentrated up to 20 mg/mL and buffer exchanged into 20 mmol/L tris, 150 mmol/L arginine buffer pH 7.0.

The buffer exchanged pool (DF pool) was loaded with 625 g antibody/m². The feed flow rate was operated at a constant rate of 250 LMH (L/m²/hour) and then reduced to 80 LMH when the retentate volume reached the value that corresponds to protein concentration of 60 g/L. The TMP was controlled at 1.0 bar until the retentate pressure control valve came to a fully open. The ultrafiltration process was operated with the permeate side open-ended. The operation was terminated when the feed pressure exceeded 3.5 bar. After ultrafiltration processing, the concentrated solution was circulated with the permeate side closed for 15 minutes under a constant feed flow rate of 10 mL/min and then recovered into a graduated cylinder. The recovered pool was stirred until visually homogeneous.

For protein concentration measurement, the recovered pool was diluted gravimetrically using a density value measured by a density meter DMA 4500 (Anton Paar, Austria). UV absorbance at 280 nm was measured with a UV/Vis spectrophotometer DU800 (Beckman Coulter, US).

Figure 19:
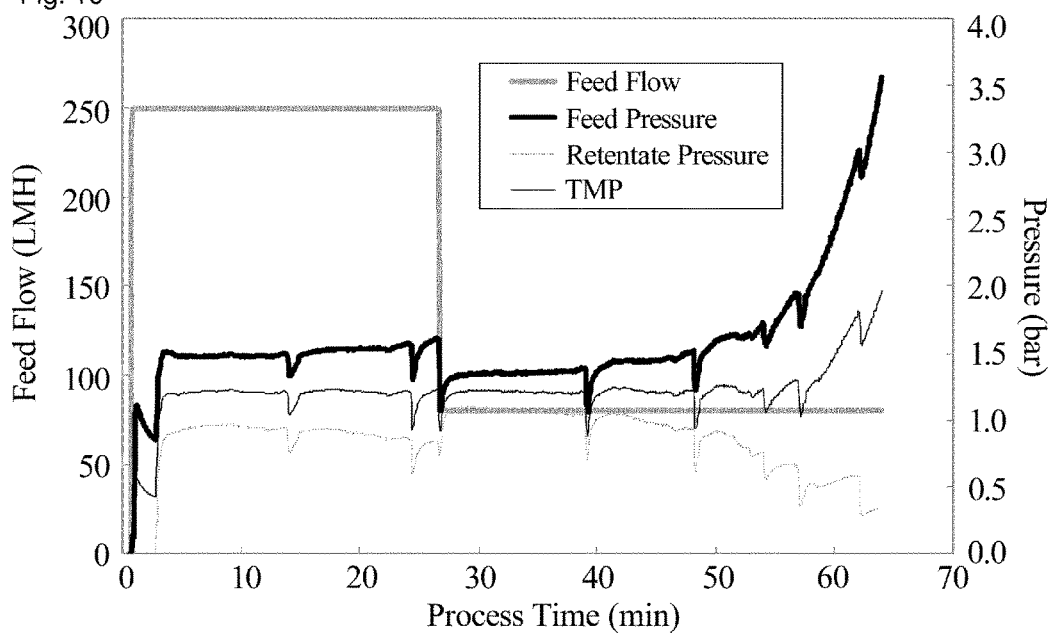
FIG. 19 demonstrates the measured process values over time for the feed flow rate, feed pressure, retentate pressure, TMP. The feed flow rate was operated at a constant rate of 250 LMH (L/m$^2$/hour) and then reduced to 80 LMH when the retentate volume reached the value that corresponds to protein concentration of 60 g/L.

FIG. 19 shows the measured process values over time for the feed flow rate, feed pressure, retentate pressure, TMP. TABLE 20 shows the result of protein concentration measurement.

TABLE 20

|  | Protein concentration (g/L) |
| --- | --- |
| DF pool | 20.6 |
| Recovered pool | 222 |

Example 14

Comparative Example 13 was repeated with the following exception. The feed flow rate was reduced to 80 LMH when the feed pressure exceeded 3.5 bar. The value of the retentate volume at that point corresponds to protein concentration of 145 g/L.

Figure 20:
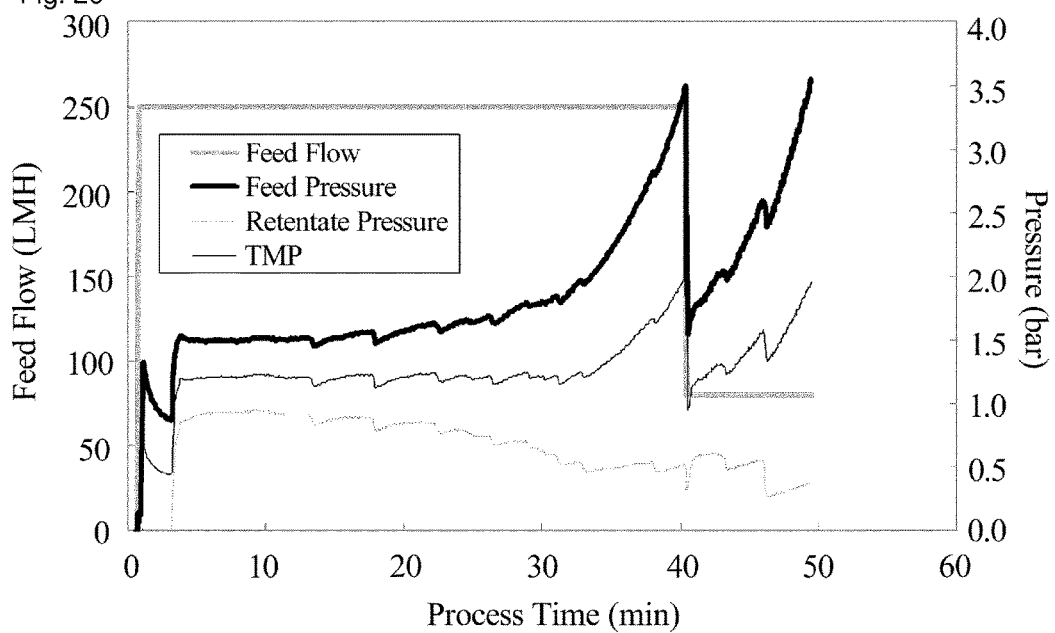
FIG. 20 demonstrates the measured process values over time for the feed flow rate, feed pressure, retentate pressure, TMP. The feed flow rate was reduced to 80 LMH when the feed pressure exceeded 3.5 bar. The value of the retentate volume at that point corresponds to protein concentration of 145 g/L.

FIG. 20 shows the measured process values over time for the feed flow rate, feed pressure, retentate pressure, TMP. TABLE 21 shows the result of protein concentration measurement.

TABLE 21

|  | Protein concentration (g/L) |
| --- | --- |
| DF pool | 21.7 |
| Recovered pool | 236 |

Example 15

Example 14 was repeated with the following exception. Once the feed pressure exceeded 3.5 bar under a constant feed flow rate of 250 LMH, the feed flow rate was set to automatic flow control in a manner to maintain the feed pressure of 3.5 bar. The operation was terminated when the feed flow rate decreased to 80 LMH.

Figure 21:
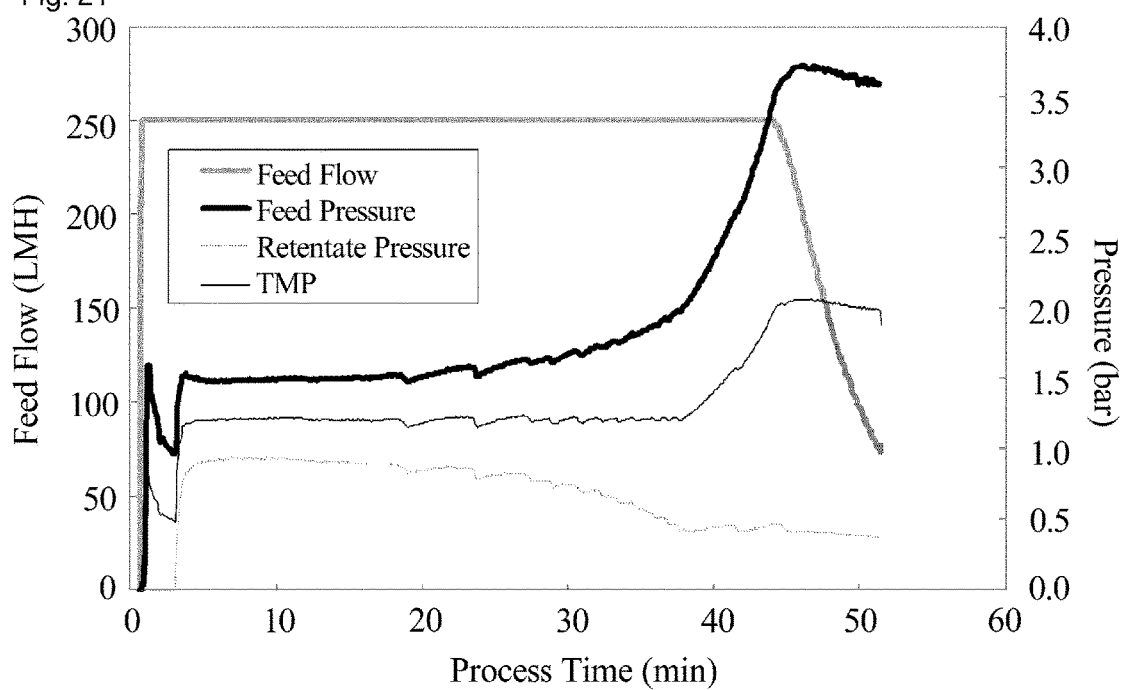
FIG. 21 demonstrates the measured process values over time for the feed flow rate, feed pressure, retentate pressure, TMP. Once the feed pressure exceeded 3.5 bar under a constant feed flow rate of 250 LMH, the feed flow rate was set to automatic flow control in a manner to maintain the feed pressure of 3.5 bar. The operation was terminated when the feed flow rate decreased to 80 LMH.

FIG. 21 shows the measured process values over time for the feed flow rate, feed pressure, retentate pressure, TMP. TABLE 22 shows the result of protein concentration measurement.

TABLE 22

|  | Protein concentration (g/L) |
| --- | --- |
| DF pool | 20.4 |
| Recovered pool | 246 |

The invention claimed is:

1. A method for preparing a composition comprising highly concentrated antibodies by ultrafiltration, wherein the method comprises the steps of: concentrating an antibody preparation by ultrafiltrating the preparation, said ultrafiltrating comprising:
    1) regulating a feed flow rate of the preparation to allow a value of a feed pressure applied to an ultrafiltration membrane to increase to 85-100% of a specified maximum feed pressure of the ultrafiltration membrane; and
    2) decreasing the feed flow rate to maintain or decrease the value of the feed pressure applied to the ultrafiltration membrane after step (1),
        wherein the feed flow rate in step (1) is maintained at 250 LMH (L/m²/hour) or higher and the feed flow rate in step (2) is decreased to 80LMH (L/m²/hour) or lower and wherein the antibody preparation directly after said ultrafiltrating has an antibody concentration above 200 g/L or a viscosity above 10 mPas.

2. The method of claim 1, wherein the antibody preparation is ultrafiltrated at ambient temperature.

3. The method of claim 1, wherein the antibody preparation is ultrafiltrated at a temperature from 10 to 30 degrees C.

4. The method of claim 1, wherein the antibody preparation is ultrafiltrated at a temperature from 15 to 30 degrees C.

5. The method of claim 1, wherein the concentrated preparation has the antibody concentration above 250 g/L or the viscosity above 40 mPa.s.

6. The method of claims 1, wherein the feed flow rate in step (1) is maintained at a constant rate.

7. The method of claim 1, wherein the maximum value of the feed pressure applied to the ultrafiltration membrane in step (1) is from 2.0 bar to 4.0 bar.

8. The method of claim 1, wherein the maximum value of the feed pressure applied to the ultrafiltration membrane in step (1) is 3.5 bar.

9. The method of claim 1, wherein step (1) is transitioned to step (2) when the retentate solution is concentrated to a protein concentration greater than 200 g/L.

10. The method of claim 1, wherein step (1) is transitioned to step (2) when the retentate solution is concentrated to a protein concentration equal or greater than 220 g/L.

11. The method of claim 1, wherein step (1) is transitioned to step (2) when the retentate solution is concentrated to a protein concentration equal to 240 g/L.

12. The method of claim 1, wherein the feed flow rate after the value of the feed pressure is decreased in step (2) is maintained at a constant rate.

13. The method of claim 1, wherein the value of the feed pressure applied to an ultrafiltration membrane in step (2) is maintained at a constant value.

14. The method of claim 1, wherein the value of the feed pressure applied to an ultrafiltration membrane in step (2) is maintained within 85-100% of the specified maximum feed pressure of the ultrafiltration membrane by reducing the feed flow rate.

15. The method of claim 13 or 14, wherein the feed flow rate is automatically regulated in a manner to maintain the feed pressure within 85-100% of the specified maximum feed pressure of the ultrafiltration membrane by a feedback control between a feed pressure and a feed flow rate.

16. The method of claim 1, further comprising between step (1) and step (2), the following step of:
3) recirculating the antibody preparation through the membrane with a permeate valve closed.

17. The method of claim 16, wherein the antibody preparation is recirculated with a retentate pressure control valve fully open.

18. The method of claim 16, wherein the feed flow rate in step (3) is maintained at a constant flow rate between 5 to 120 m LMH (L/m$^2$/hour).

19. The method of claim 16, wherein the feed flow rate in step (3) is maintained at a constant flow rate between 10 to 80 LMH (L/m$^2$/hour).

20. The method of claim 1, wherein the buffer composition of the antibody preparation is between 10 to 30 mmol/L histidine.

21. The method of claim 1, wherein the buffer composition of the antibody preparation is 20 mmol/L histidine.

22. The method of claim 1, wherein the pH of the antibody preparation is between pH 3.0 and pH 10.0.

23. The method of claim 1, wherein the pH of the antibody preparation is between pH 5.5 and pH 6.5.

24. The method of claim 1, wherein the pH of the antibody preparation is pH 6.0.

25. The method of claim 1, wherein the ultrafiltration membrane has a molecular weight cut off of 50 kDa or less.

26. The method of claim 1, wherein the ultrafiltration membrane has a molecular weight cut off of 30 kDa or less.

27. The method of claim 1, wherein the composition comprises highly concentrated anti-human interleukin-6 receptor monoclonal antibodies.

28. The method of claim 27, wherein the composition comprises highly concentrated tocilizumab.

29. A method for preparing a composition comprising highly concentrated proteins by ultrafiltration, wherein the method comprises the steps of: concentrating a protein preparation by ultrafiltrating the preparation, said ultrafiltrating comprising:
1) regulating a feed flow rate of the preparation to allow a value of a feed pressure applied to an ultrafiltration membrane to increase to 85-100% of a specified maximum feed pressure of the ultrafiltration membrane; and
2) decreasing the feed flow rate to maintain or decrease the value of the feed pressure applied to the ultrafiltration membrane after step (1),
wherein the feed flow rate in step (1) is maintained at 250 LMH (L/m$^2$/hour) or higher and the feed flow rate in step (2) is decreased to 80 LMH (L/m$^2$/hour) or lower and wherein the protein preparation directly after said ultrafiltrating has a protein concentration above 200 g/L or a viscosity above 10 mPas.

* * * * *

UNITED STATES PATENT AND TRADEMARK OFFICE
CERTIFICATE OF CORRECTION

PATENT NO. : 9,630,988 B2
APPLICATION NO. : 14/241567
DATED : April 25, 2017
INVENTOR(S) : Kelby Lau et al.

Page 1 of 1

It is certified that error appears in the above-identified patent and that said Letters Patent is hereby corrected as shown below:

In the Claims

Column 20, Claim 1, Line 12, "comprises the steps of: concentrating" should be --comprises concentrating--.

Column 20, Claim 1, Line 28, "mPas" should be --mPa·s--.

Column 22, Claim 29, Line 12, "comprises the steps of: concentrating" should be --comprises concentrating--.

Column 22, Claim 29, Line 27, "mPas" should be --mPa·s--.

Signed and Sealed this
Twelfth Day of September, 2017

Joseph Matal
*Performing the Functions and Duties of the
Under Secretary of Commerce for Intellectual Property and
Director of the United States Patent and Trademark Office*